(12) United States Patent
Yaffe et al.

(10) Patent No.: US 12,172,000 B2
(45) Date of Patent: Dec. 24, 2024

(54) CONNECTORS FOR HIGH DENSITY NEURAL INTERFACES

(71) Applicant: Verily Life Sciences LLC, South San Francisco, CA (US)

(72) Inventors: Benjamin K. Yaffe, South San Francisco, CA (US); Ken Rys, South San Francisco, CA (US); Bo Lu, South San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 235 days.

(21) Appl. No.: 17/622,561

(22) PCT Filed: Jun. 5, 2020

(86) PCT No.: PCT/US2020/036362
§ 371 (c)(1),
(2) Date: Dec. 23, 2021

(87) PCT Pub. No.: WO2020/263535
PCT Pub. Date: Dec. 30, 2020

(65) Prior Publication Data
US 2022/0265998 A1  Aug. 25, 2022

Related U.S. Application Data

(60) Provisional application No. 62/866,401, filed on Jun. 25, 2019.

(51) Int. Cl.
*A61N 1/05* (2006.01)
*A61N 1/375* (2006.01)
(52) U.S. Cl.
CPC ......... *A61N 1/0534* (2013.01); *A61N 1/3754* (2013.01)

(58) Field of Classification Search
CPC .. A61N 1/0534; A61N 1/3754; A61N 1/3752; A61N 1/0551
See application file for complete search history.

(56) References Cited

U.S. PATENT DOCUMENTS

| | | | | | |
|---|---|---|---|---|---|
| 5,547,399 | A | * | 8/1996 | Naghi | H01R 27/00 D13/133 |
| 5,632,770 | A | * | 5/1997 | Schaldach | A61B 5/283 607/129 |

(Continued)

FOREIGN PATENT DOCUMENTS

| | | |
|---|---|---|
| RU | 2012120108 | 11/2013 |
| WO | 2014186122 | 11/2014 |

OTHER PUBLICATIONS

Application No. PCT/US2020/036362, International Search Report and Written Opinion, Mailed On Sep. 3, 2020, 8 pages.

*Primary Examiner* — Lynsey C Eiseman
(74) *Attorney, Agent, or Firm* — Kilpatrick Townsend & Stockton LLP

(57) ABSTRACT

The present disclosure relates to connectors for high density neural interfaces and methods of microfabricating the connectors. Particularly, aspects of the present disclosure are directed to a connector having a main body, a first plug extending from the main body, a flexible bridge extending from the main body or the first plug, and a second plug extending from the flexible bridge. This structure allows for the main body, the first plug, and the second plug to be arranged in tandem on a longitudinal axis of the main body, which enables the connector to be passed through a narrow diameter cannula. This structure also allows for the first plug and the second plug to be arranged in a spread out orientation, which enables the connector to be electrically connected with a neurostimulator.

20 Claims, 17 Drawing Sheets

(56) References Cited

U.S. PATENT DOCUMENTS

| | | | | |
|---|---|---|---|---|
| 6,217,369 | B1* | 4/2001 | Shchervinsky | H01R 11/12 |
| | | | | 439/456 |
| 6,269,272 | B1* | 7/2001 | Fischer, Sr. | A61N 1/0573 |
| | | | | 607/127 |
| 9,474,894 | B2 | 10/2016 | Mercanzini et al. | |
| 2005/0049655 | A1* | 3/2005 | Boveja | A61N 1/36071 |
| | | | | 607/58 |
| 2008/0039917 | A1* | 2/2008 | Cross | A61N 1/05 |
| | | | | 607/122 |
| 2010/0057176 | A1* | 3/2010 | Barker | A61N 1/0551 |
| | | | | 607/117 |
| 2011/0009932 | A1* | 1/2011 | McDonald | A61N 1/0551 |
| | | | | 607/116 |
| 2013/0085361 | A1* | 4/2013 | Mercanzini | A61B 5/4041 |
| | | | | 600/377 |
| 2016/0113710 | A1* | 4/2016 | Ogle | A61M 25/0012 |
| | | | | 606/41 |

* cited by examiner w-w or m-m w-w or m-m

CONNECTORS FOR HIGH DENSITY NEURAL INTERFACES

CROSS-REFERENCE TO RELATED APPLICATION

The present application is a national phase filing of International Patent Application No. PCT/US2020/036362, filed Jun. 5, 2020, which claims priority and benefit from U.S. Provisional Application No. 62/866,401, filed Jun. 25, 2019, the entire contents of which are incorporated herein by reference for all purposes.

FIELD

The present disclosure relates to implantable neuromodulation devices and methods of fabrication, and in particular to connectors for high density neural interfaces and methods of microfabricating the connectors.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically consist of an implant comprising a neurostimulator having electronics connected to a lead assembly that delivers electrical pulses to electrodes interfaced with nerves or nerve bundles via an electrode assembly. The lead assembly is typically formed of a conductive material and takes the form of an insulated wire (e.g., a dedicated channel) connected to the electrodes via a first connector on one end (e.g., a distal end) and the electronics of the neurostimulator via a second connector on another end (e.g., a proximal end). In some instances (e.g., deep implants), the lead assembly comprises additional conductors and connectors such as extension wires or a cable connected via connectors between the electrodes and the electronics of the neurostimulator.

Conventional neuromodulation devices include between four and sixteen electrodes, and thus typically include four to sixteen channels or wires connected respectively to the electrodes at the distal end and the electronics of the neurostimulator at the proximal end. However, there is a need for high density neural interfaces that include greater than sixteen electrodes to interface with larger tissue volumes, to recruit smaller populations of neurons for recording, or to provide more targeted therapy by tailoring the electrical stimulation parameters and activated tissue volume. Increasing the density or number of electrodes can increase the number of channels or wires needed to connect the electrodes and the electronics of the neurostimulator. In order to implement high channel or wire counts, there is a need for reliable electrical connections that can maintain contact and electrical isolation in a subject body (e.g., a patient body) for many years. Typically, a lead assembly containing a high channel or wire count needs to be permanently connected to the electronics. However, this is not ideal because the electronics need to be replaced every few years to upgrade them or to replace batteries, and surgeons have a strong preference not to remove the lead assembly from the neural tissue due to the risk to the patient. Therefore, there is a need for reliable and non-permanent connectors for lead assemblies having high density neural interfaces.

BRIEF SUMMARY

In various embodiments, a connector is provided for that comprises: a main body comprising a first supporting structure and a plurality of conductive traces formed on the first supporting structure; a first plug extending from the main body, the first plug comprising: a second supporting structure, a first set of conductive traces extending from the plurality of conductive traces and formed on the second supporting structure, and a first set of conductive contacts formed on the second supporting structure, where the first set of conductive contacts are electrically connected to the first set of conductive traces; a flexible bridge extending from the main body, the flexible bridge comprising: a third supporting structure, and a second set of conductive traces extending from the plurality of conductive traces and formed on the third supporting structure; and a second plug extending from the flexible bridge, the second plug comprising: a fourth supporting structure, the second set of conductive traces extending from the plurality of conductive traces and formed on the fourth supporting structure, and a second set of conductive contacts formed on the fourth supporting structure, where the second set of conductive contacts are electrically connected to the second set of conductive traces.

In some embodiments, the first supporting structure, the second supporting structure, the third supporting structure, the fourth supporting structure, or a combination thereof are formed of one or more layers of dielectric material.

In some embodiments, the first supporting structure, the second supporting structure, the third supporting structure, and the fourth supporting structure are monolithic and formed of one or more layers of dielectric material.

In some embodiments, the dielectric material is a polymer of imide monomers, a liquid crystal polymer (LCP), parylene, polyether ether ketone (PEEK), or a combination thereof.

In some embodiments, the plurality of conductive traces, the first set of conductive traces, and the second set of conductive traces are comprised of one or more layers of conductive material, and the conductive material is platinum (Pt), platinum/iridium (Pt/Ir), titanium (Ti), gold/titanium (Au/Ti), or any alloy thereof.

In some embodiments, the first set of conductive contacts and the second set of conductive contacts are comprised of one or more layers of conductive material, and the conductive material is platinum (Pt), platinum/iridium (Pt/Ir), titanium (Ti), gold/titanium (Au/Ti), or any alloy thereof.

In some embodiments, the second supporting structure and the fourth supporting structure are formed of one or more layers of dielectric material; the one or more layers of dielectric material comprise a first layer of dielectric material and a second layer of dielectric material; the first set of conductive traces are buried between the first layer of dielectric material and the second layer of dielectric material of the first plug; and the second set of conductive traces are buried between the first layer of dielectric material and the second layer of dielectric material of the second plug.

In some embodiments, the first plug and the second plug are a cylindrical tube; and the cylindrical tube comprises: (i) the one or more layers of dielectric material, where the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube.

In some embodiments, the one or more layers of dielectric material are at least partially wrapped around the core.

In some embodiments, the first layer of dielectric material is a high temperature liquid crystal polymer, and the second layer of dielectric material is a low temperature liquid crystal polymer.

In some embodiments, the core is comprised of one or more layers of material such that the core has a hardness measured by a Shore A durometer of greater than 70 A.

In some embodiments, the third supporting structure is formed of one or more layers of dielectric material and the flexible bridge has a hardness, measured by a Shore A durometer, that is less than a hardness, measured by the Shore A durometer, of the first plug and the second plug.

In some embodiments, the flexible bridge has a length that is greater than a length of the first plug.

In some embodiments, the flexible bridge is a helical structure.

In some embodiments, the flexible bridge is wrapped in a helical manner around the first plug.

In some embodiments, the connector further comprises a silicone sleeve placed over the flexible bridge.

In various embodiments, a lead assembly is provided that comprises: a cable comprising a proximal end, a distal end, a first supporting structure, a first set of conductive traces formed on the first supporting structure, and a second set of conductive traces formed on the first supporting structure; a first plug extending from the proximal end of the cable, where the first plug comprises: a second supporting structure and a first set of conductive contacts formed on the second supporting structure, and where the first set of conductive contacts are electrically connected to the first set of conductive traces; a flexible bridge extending from the proximal end of the cable, where the flexible bridge comprises: a third supporting structure, and the second set of conductive traces extending from the cable and formed on the third supporting structure; and a second plug extending from the flexible bridge, where the second plug comprises: a fourth supporting structure and a second set of conductive contacts formed on the fourth supporting structure, and where the second set of conductive contacts are electrically connected to the second set of conductive traces.

In some embodiments, the lead assembly further comprises an electrode assembly located at the distal end of the cable, the electrode assembly comprising electrodes electrically connected to the first set of conductive traces and the second set of conductive traces.

In some embodiments, the first supporting structure, the second supporting structure, the third supporting structure, the fourth supporting structure, or a combination thereof are formed of one or more layers of dielectric material.

In some embodiments, the first supporting structure, the second supporting structure, the third supporting structure, and the fourth supporting structure are monolithic and formed of one or more layers of dielectric material.

In some embodiments, the dielectric material is a polymer of imide monomers, a liquid crystal polymer (LCP), parylene, polyether ether ketone (PEEK), or a combination thereof.

In some embodiments, the first set of conductive traces and the second set of conductive traces are comprised of one or more layers of conductive material, and the conductive material is platinum (Pt), platinum/iridium (Pt/Ir), titanium (Ti), gold/titanium (Au/Ti), or any alloy thereof.

In some embodiments, the first set of conductive contacts and the second set of conductive contacts are comprised of one or more layers of conductive material, and the conductive material is platinum (Pt), platinum/iridium (Pt/Ir), titanium (Ti), gold/titanium (Au/Ti), or any alloy thereof.

In some embodiments, the second supporting structure and the fourth supporting structure are formed of one or more layers of dielectric material; the one or more layers of dielectric material comprise a first layer of dielectric material and a second layer of dielectric material; the first set of conductive traces are buried between the first layer of dielectric material and the second layer of dielectric material of the first plug; and the second set of conductive traces are buried between the first layer of dielectric material and the second layer of dielectric material of the second plug.

In some embodiments, the first plug and the second plug are a cylindrical tube; and the cylindrical tube comprises: (i) the one or more layers of dielectric material, where the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube.

In some embodiments, the one or more layers of dielectric material are at least partially wrapped around the core.

In some embodiments, the first layer of dielectric material is a high temperature liquid crystal polymer, and the second layer of dielectric material is a low temperature liquid crystal polymer.

In some embodiments, the core is comprised of one or more layers of material such that the core has a hardness measured by a Shore A durometer of greater than 70 A.

In some embodiments, the third supporting structure is formed of one or more layers of dielectric material, and the flexible bridge has a hardness, measured by a Shore A durometer, that is less than a hardness, measured by the Shore A durometer, of the first plug and the second plug.

In some embodiments, the flexible bridge has a length that is greater than a length of the first plug.

In some embodiments, the flexible bridge is a helical structure.

In some embodiments, the flexible bridge is wrapped in a helical manner around the first plug.

In some embodiments, the lead assembly further comprises a silicone sleeve placed over the flexible bridge.

In various embodiments, a connector is provided that comprises: a main body comprising a first supporting structure and a plurality of conductive traces formed on the first supporting structure; a first plug extending from the main body, the first plug comprising: a second supporting structure, a first set of conductive traces extending from the plurality of conductive traces and formed on the second supporting structure, a second set of conductive traces extending from the plurality of conductive traces and formed on the second supporting structure, and a first set of conductive contacts formed on the second supporting structure, where the first set of conductive contacts are electrically connected to the first set of conductive traces; a flexible bridge extending from the first plug, the flexible bridge comprising: a third supporting structure, and the second set of conductive traces extending from the first plug and formed on the third supporting structure; and a second plug extending from the flexible bridge, the second plug comprising: a fourth supporting structure, the second set of conductive traces extending from the flexible bridge and formed on the fourth supporting structure, and a second set of conductive contacts formed on the fourth supporting structure, where the second set of conductive contacts are electrically connected to the second set of conductive traces.

In some embodiments, the connector further comprises a clamshell receiver that that holds the main body, the first plug, the flexible bridge, and the second plug in a pattern.

In some embodiments, the pattern comprises the flexible bridge positioned such that the first plug and the second plug are aligned on a same plane.

In some embodiments, the first supporting structure, the second supporting structure, the third supporting structure, the fourth supporting structure, or a combination thereof are formed of one or more layers of dielectric material.

In some embodiments, the first supporting structure, the second supporting structure, the third supporting structure, and the fourth supporting structure are monolithic and formed of one or more layers of dielectric material.

In some embodiments, the dielectric material is a polymer of imide monomers, a liquid crystal polymer (LCP), parylene, polyether ether ketone (PEEK), or a combination thereof.

In some embodiments, the plurality of conductive traces, the first set of conductive traces, and the second set of conductive traces are comprised of one or more layers of conductive material, and the conductive material is platinum (Pt), platinum/iridium (Pt/Ir), titanium (Ti), gold/titanium (Au/Ti), or any alloy thereof.

In some embodiments, the first set of conductive contacts and the second set of conductive contacts are comprised of one or more layers of conductive material, and the conductive material is platinum (Pt), platinum/iridium (Pt/Ir), titanium (Ti), gold/titanium (Au/Ti), or any alloy thereof.

In some embodiments, the second supporting structure and the fourth supporting structure are formed of one or more layers of dielectric material; the one or more layers of dielectric material comprise a first layer of dielectric material and a second layer of dielectric material; the first set of conductive traces are buried between the first layer of dielectric material and the second layer of dielectric material of the first plug; and the second set of conductive traces are buried between the first layer of dielectric material and the second layer of dielectric material of the second plug.

In some embodiments, the first plug and the second plug are a cylindrical tube; and the cylindrical tube comprises: (i) the one or more layers of dielectric material, where the first layer of dielectric material defines an outer diameter of the cylindrical tube and the second layer of dielectric material defines an inner diameter of the tube; and (ii) a core that at least partially fills an interior of the cylindrical tube defined by the inner diameter of the cylindrical tube.

In some embodiments, the one or more layers of dielectric material are at least partially wrapped around the core.

In some embodiments, the first layer of dielectric material is a high temperature liquid crystal polymer, and the second layer of dielectric material is a low temperature liquid crystal polymer.

In some embodiments, the core is comprised of one or more layers of material such that the core has a hardness measured by a Shore durometer A of greater than 70 A.

In some embodiments, the third supporting structure is formed of one or more layers of dielectric material and the flexible bridge has a hardness, measured by a Shore A durometer, that is less than a hardness, measured by the Shore A durometer, of the first plug and the second plug.

BRIEF DESCRIPTION OF THE DRAWINGS

The present invention will be better understood in view of the following non-limiting figures, in which.

DETAILED DESCRIPTION

I. Introduction

Figure 1:
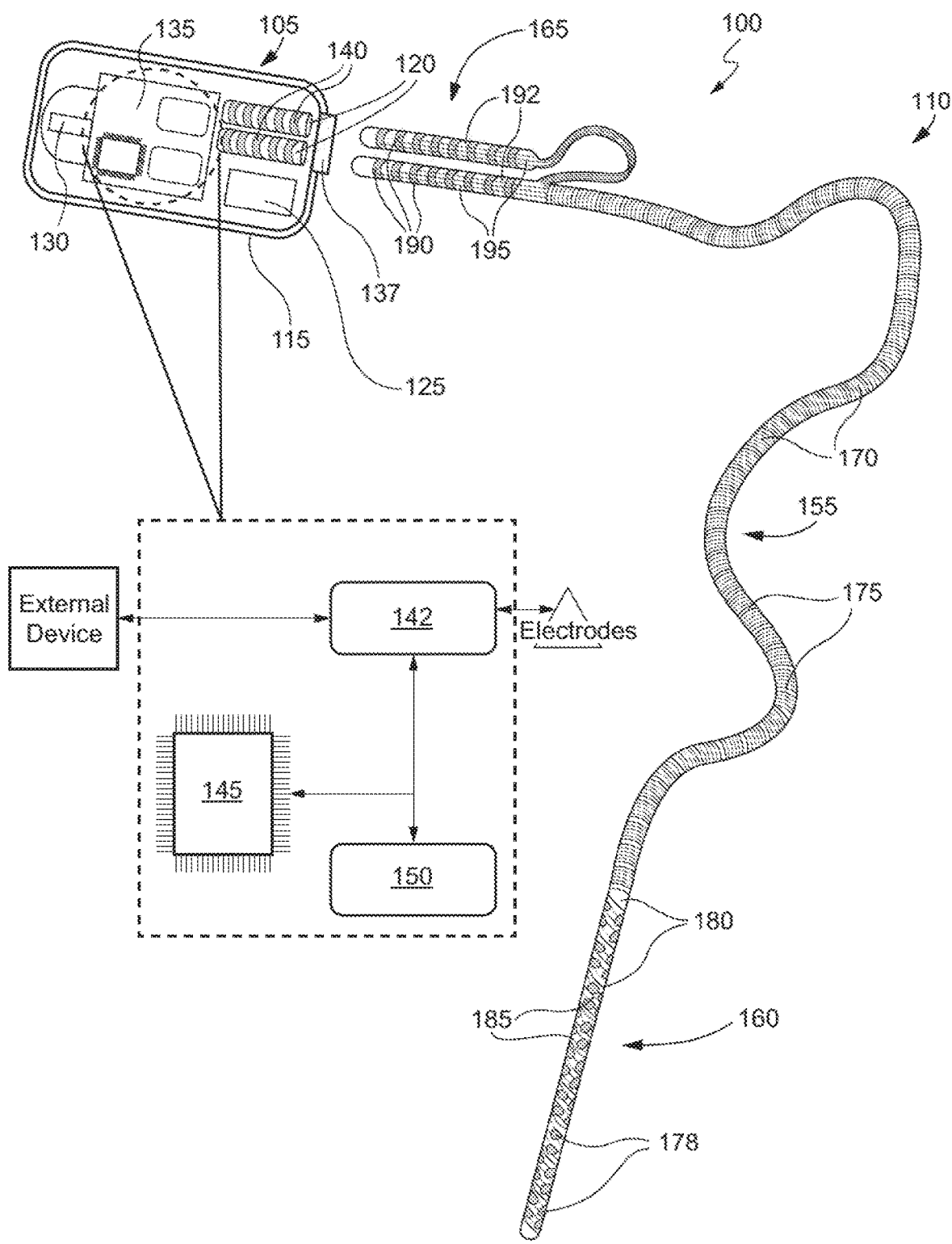
FIG. 1 shows a neuromodulation system in accordance with various embodiments.

The following disclosure describes connectors for high density neural interfaces and methods of microfabricating the connectors. In some embodiments, a connector is located at a proximal end of the lead assembly and used to connect the lead assembly with the neurostimulator. In other embodiments, one or more connectors are located at the proximal end and/or distal end of one or more lead bodies and used to connect one or more lead bodies thereby extending an overall length of the lead assembly. As used herein, the term "proximal" or "proximal end" refers to a first end of the main body, while the term "distal" or "distal end" refers to a second end opposing the first end. For example, the proximal end may be an end of the main body, which is closest to the user, and the distal end may be an end of the main body, which is furthest from the user.

The connectors may be fabricated using microfabricating techniques. In certain embodiments, a connector is fabricated as a monolithic structure. As used herein, the phrase "monolithic" refers to a device fabricated using a same layer of base material. As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 μm). Thin films may be deposited by applying a very thin film of material (e.g., between a few nanometers to about 100 μm) onto a substrate surface to be coated, or onto a previously deposited layer of thin film. In various embodiments, a thin film connector is provided comprising a base polymer body (e.g., a supporting structure) and at least one conductive trace formed on the base polymer body. As used herein, the term "high density neural interface(s)" refers to a neural interface that comprises at least sixteen electrodes (i.e., recording, sensing, stimulating, other types of electrodes, or combinations thereof).

Neuromodulation devices such as deep brain stimulators electrically interface with neural tissue and treat various neurological conditions through electrical stimulation. As described herein, conventional neuromodulation devices use between four and sixteen electrodes and comprise a neurostimulator and lead assembly containing the electrodes. The neuromodulation devices with high density neural interfaces (i.e., at least sixteen electrodes) for deep brain stimulation, cortical brain stimulation, spine stimulation, etc. often are limited in contact count by lead density, implant technique, connector density/pitch/size, or complexity (e.g., having a lead split to multiple connectors). However, higher density arrays are desired due to the ability to more closely focus energy during therapy in order to increase clinical effectiveness, reduce side effects due to errant charge, and increase battery life by using charge more efficiently.

Specifically, deep brain stimulation is a neurostimulation therapy that could greatly benefit from higher density arrays. However, due to the standard deep brain stimulation implant technique, where the lead is implanted through a rigid metal trans-cranial precise stereotactic placement cannula, such leads are unusable for human implant. The reason is that the proximal end of such high density leads must necessarily be very large, either due to an excess of conventional sealable contacts, or due to the presence of a multiplexer chip. Both of these factors necessarily increase the lead assembly's maximum outer diameter, require multiple branched connectors, or other solutions that do not fit within the standard narrow diameter of the cannula used in deep brain stimulation implant techniques. Excess diameter is not justified, as the larger the maximum diameter of lead, the more brain tissue is damaged/destroyed during implant. Moreover, modifying the implant procedure and cannula leads to fundamental friction in implementation and commercialization.

To address these limitations and problems, the connectors of the present embodiments include multiple sections of conductive contacts that can be arranged in tandem to fit through the lumen of cannulas typically employed for deep brain implants, and subsequently re-arranged post implant such that the proximal contacts can be connected with a header of a neurostimulator. One illustrative embodiment of the present disclosure is directed to a connector having a main body, a first plug extending from the main body, a flexible bridge extending from the main body or the first plug, and a second plug extending from the flexible bridge. This structure allows for the main body, the first plug, and the second plug to be arranged in tandem on a longitudinal axis of the main body, which enables the connector to be passed through a narrow diameter cannula. This structure also allows for the first plug and the second plug to be arranged in a spread out orientation, which enables the connector to be electrically connected with a neurostimulator.

In other embodiments, a connector is provided that comprises: (a) a main body including (i) a first supporting structure and (ii) a plurality of conductive traces formed on the first supporting structure, and (b) a first plug extending from the main body, the first plug including: (i) a second supporting structure, (ii) a first set of conductive traces extending from the plurality of conductive traces and formed on the second supporting structure, and (iii) a first set of conductive contacts formed on the second supporting structure. The first set of conductive contacts are electrically connected to the first set of conductive traces. The connector further comprises (c) a first plug extending from the main body, the first plug including: (i) a second supporting structure, (ii) a first set of conductive traces extending from the plurality of conductive traces and formed on the second supporting structure, and (iii) a first set of conductive contacts formed on the second supporting structure. The first set of conductive contacts are electrically connected to the first set of conductive traces. The connector further comprises (d) a flexible bridge extending from the main body, the flexible bridge comprising: (i) a third supporting structure, and (ii) a second set of conductive traces extending from the plurality of conductive traces and formed on the third supporting structure. The connector further comprises (e) a second plug extending from the flexible bridge, the second plug comprising: (i) a fourth supporting structure, (ii) the second set of conductive traces extending from the plurality of conductive traces and formed on the fourth supporting structure, and (iii) a second set of conductive contacts formed on the fourth supporting structure. The second set of conductive contacts are electrically connected to the second set of conductive traces.

In other embodiments, a lead assembly is provided that comprises (a) a cable including a proximal end, a distal end, a first supporting structure, a first set of conductive traces formed on the first supporting structure, and a second set of conductive traces formed on the first supporting structure. The lead assembly further comprises (b) a first plug extending from the proximal end of the cable. The first plug includes: (i) a second supporting structure and (ii) a first set of conductive contacts formed on the second supporting structure, and where the first set of conductive contacts are electrically connected to the first set of conductive traces. The lead assembly further comprises (c) a flexible bridge extending from the proximal end of the cable. The flexible bridge includes: (i) a third supporting structure, and (ii) the second set of conductive traces extending from the cable and formed on the third supporting structure. The lead assembly further comprises (d) a second plug extending from the flexible bridge. The second plug includes: (i) a fourth supporting structure and (ii) a second set of conductive contacts formed on the fourth supporting structure, and where the second set of conductive contacts are electrically connected to the second set of conductive traces.

In other embodiments, a connector is provided that comprises (a) a main body, (b) a first plug extending from the main body, (c) a flexible bridge extending from the first plug, (d) a second plug extending from the flexible bridge, and (e) a clamshell receiver that that holds the main body, the first plug, the flexible bridge, and the second plug in a pattern. The main body includes a first supporting structure and a plurality of conductive traces formed on the first supporting structure. The first plug includes: (i) a second supporting structure, (ii) a first set of conductive traces extending from the plurality of conductive traces and formed on the second supporting structure, (iii) a second set of conductive traces extending from the plurality of conductive traces and formed on the second supporting structure, and (iv) a first set of conductive contacts formed on the second supporting structure. The first set of conductive contacts are electrically connected to the first set of conductive traces. The flexible bridge includes: (i) a third supporting structure, and (ii) the second set of conductive traces extending from the first plug and formed on the third supporting structure. The second plug includes: (i) a fourth supporting structure, (ii) the second set of conductive traces extending from the flexible bridge and formed on the fourth supporting structure, and (iii) a second set of conductive contacts formed on the fourth supporting structure. The second set of conductive contacts are electrically connected to the second set of conductive traces.

Advantageously, these approaches provide a connector, which has increased contact points, a smaller footprint, and greater design flexibility. More specifically, these approaches enable connectors with reliable, non-permanent connections between a lead assembly and a neurostimulator. This solution is scalable to connecting many electrodes (e.g., greater than sixteen) (optionally using a multiplexer chip), and thus enabling several therapeutic opportunities for neurostimulation. Furthermore even for applications where multiple electrodes are not required, various embodiments can be miniaturized to make the implant minimally invasive, additionally may make invasive anatomies to become accessible (or navigable) due to the miniaturization. It should be understood that although deep brain neurostimulation device applications are provided as examples of some embodiments, this solution is applicable to all leads and devices that need electrodes/sensors attached to a neurostimulator.

Neuromodulation Devices and Systems with a Lead Assembly

FIG. 1 shows a neuromodulation system 100 in accordance with some aspects of the present invention. In various embodiments, the neuromodulation system 100 includes an implantable neurostimulator 105 and a lead assembly 110. The implantable neurostimulator 105 (e.g., an implantable pulse generator (IPG)) may include a housing 115, a feedthrough assembly or header 120, a power source 125, an antenna 130, and an electronics module 135 (e.g., a computing system). The housing 115 may be comprised of materials that are biocompatible such as bioceramics or bioglasses for radio frequency transparency, or metals such as titanium. In accordance with some aspects of the present invention, the size and shape of the housing 115 may be selected such that the neurostimulator 105 can be implanted within a patient. In the example shown in FIG. 1, the feedthrough assembly or header 120 is attached to a hole 137 in a surface of the housing 115 such that the housing 115 is hermetically sealed. The feedthrough assembly or header 120 may include one or more contacts 140 (i.e., electrically conductive elements, pins, wires, tabs, pads, etc.) mounted within the housing 115 or a cap extending from an interior to an exterior of the housing 115. The one or more contacts 140 are arranged to match and make electrical contact with one or more contacts of a connector of the lead assembly 110. In various embodiments, the contacts 140 may be made with a hemisphere on contact (point contact) or with a cylinder on contact (line contact). In some embodiments, the contacts 140 are spring-loaded normal to the outer contact surfaces of the contacts of the connector. The power source 125 may be within the housing 115 and connected (e.g., electrically connected) to the electronics module 135 to power and operate the components of the electronics module 135. The antenna 130 may be connected (e.g., electrically connected) to the electronics module 135 for wireless communication with external devices via, for example, radiofrequency (RF) telemetry. A used herein, "electrically connected" or "electrically interfaced" means an electrical circuit (path or line through which an electrical current flows) is created between the two or more components that are connected or interfaced. The connection or interface between the two or more components may be permanent or temporary.

In some embodiments, the electronics module 135 may be connected (e.g., electrically connected) to interior ends of the feedthrough assembly 120 such that the electronics module 135 is able to apply a signal or electrical current to conductive traces of the lead assembly 110 connected to the feedthrough assembly 120. The electronics module 135 may include discrete and/or integrated electronic circuit components that implement analog and/or digital circuits capable of producing the functions attributed to the neuromodulation devices or systems such as applying or delivering neural stimulation to a patient. In various embodiments, the electronics module 135 may include software and/or electronic circuit components such as a pulse generator 142 that generates a signal to deliver a voltage, current, optical, or ultrasonic stimulation to a nerve or artery/nerve plexus via electrodes, a controller 145 that determines or senses electrical activity and physiological responses via the electrodes and sensors, controls stimulation parameters of the pulse generator 140 (e.g., control stimulation parameters based on feedback from the physiological responses), and/or causes delivery of the stimulation via the pulse generator 140 and electrodes, and a memory 150 with program instructions operable on by the pulse generator 140 and the controller 145 to perform one or more processes for applying or delivering neural stimulation.

In various embodiments, the lead assembly 110 includes one or more cables or lead bodies 155, one or more electrode assemblies 160, and one or more multi-sectioned connectors 165, as discussed in further detail herein. The one or more cables 155 may include one or more conductive traces 170 formed on a supporting structure 175. The one or more electrode assemblies 160 may include one or more electrodes 178 and/or sensors formed on a supporting structure 180 using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). The one or more electrodes 178 may be in electrical connection with one or more conductive traces 185. The one or more multi-sectioned connectors 165 may include one or more conductive contacts 190 formed on a supporting structure 192 in electrical connection with one or more conductive traces 195.

In some embodiments, the lead assembly 110 is a monolithic structure, polylithic structure, or a combinations of monolithic and polylithic structures. For example, the one or more cables or lead bodies 155, the one or more electrode assemblies 160, and the one or more multi-sectioned connectors 165 may all be fabricated using a same layer of base material (monolithic). In other words, the supporting structures 175, 180, 192 may be a continuous layer of base material (e.g., one or more layers of dielectric material). Moreover, the one or more conductive traces 170, 185, 195 may all be fabricated using the same layer of conductive material. In other words, the one or more conductive traces 170, 185, 195 may be a continuous layer of conductive material (e.g., one or more layers of conductive material). Alternatively, the one or more cables or lead bodies 155, the one or more electrode assemblies 160, and the one or more multi-sectioned connectors 165 may be fabricated using different layers or combinations of the same and different layers of base material that are connected together (polylithic or a combination of monolithic and polylithic). In other words, the supporting structures 175, 180, 192 may include various layers of base material (e.g., one or more layers of dielectric material) that interconnected together or a combination of continuous and interconnected layers of base material. Moreover, the one or more conductive traces 170, 185, 195 may all be fabricated using different layers or combinations of the same and different layers of conductive material. In other words, the one or more conductive traces 170, 185, 195 may be interconnected layers or a combination of continuous and interconnected layers of conductive material (e.g., one or more layers of conductive material).

Multi-Sectioned Connectors and Methods of Manufacture

Figure 2:
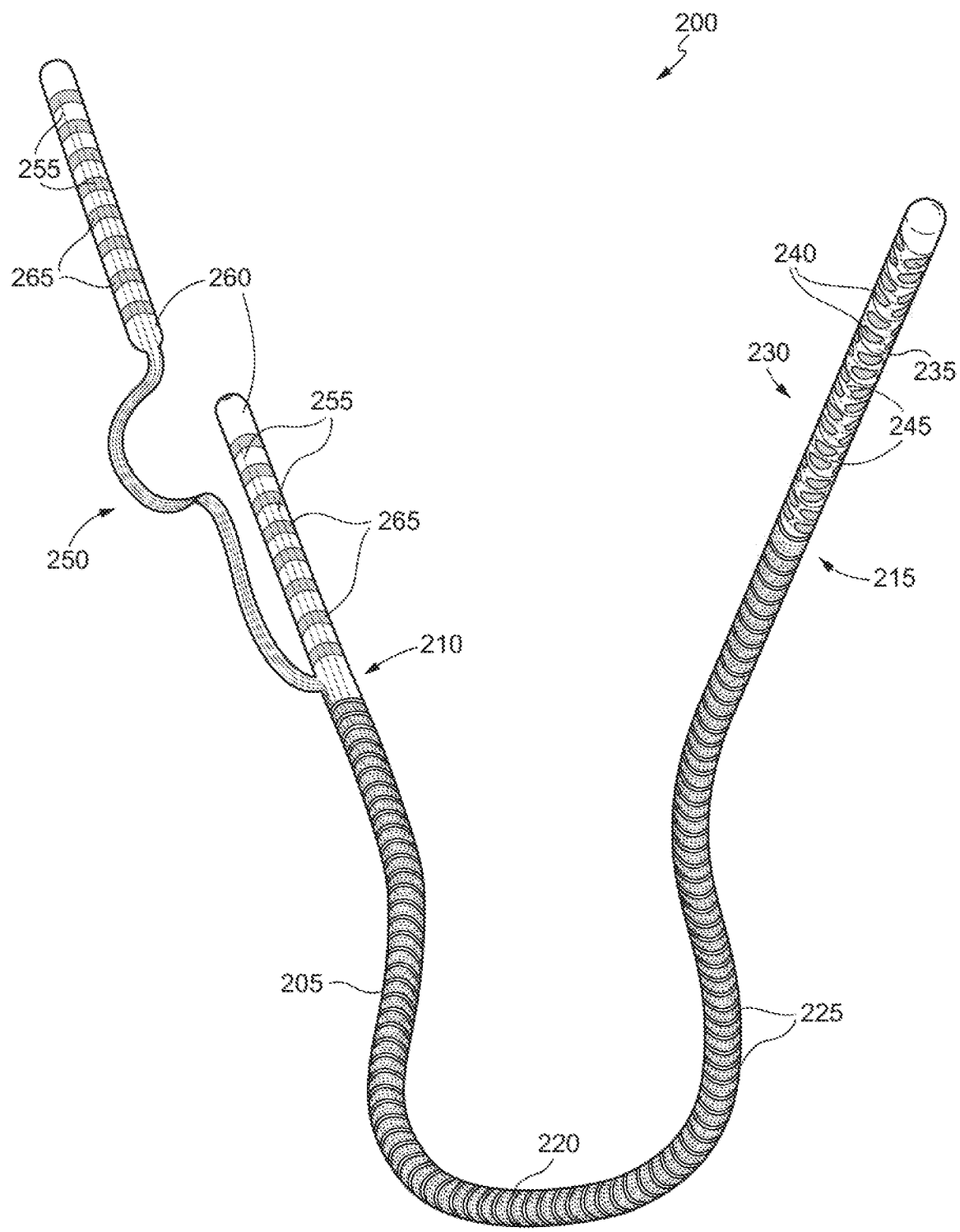
FIG. 2 shows a lead assembly in accordance with various embodiments.

FIG. 2 shows a lead assembly 200 (e.g., the lead assembly 110 described with respect to FIG. 1) in accordance with aspects of the present disclosure. In various embodiments, the lead assembly 200 comprises a cable 205 having a proximal end 210 and a distal end 215. The cable 205 may comprise a supporting structure 220 and a plurality of conductive traces 225 formed on a portion of the supporting structure 220. As used herein, the term "formed on" refers to a structure or feature that is formed on a surface of another structure or feature, a structure or feature that is formed within another structure or feature, or a structure or feature that is formed both on and within another structure or feature. In some embodiments, the supporting structure 220 extends from the proximal end 210 to the distal end 215. In some embodiments, the supporting structure 220 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 220 is made of one or more layers of dielectric material formed on a substrate. The substrate may be made from any type of metallic or non-metallic material.

In various embodiments, the plurality of conductive traces 225 are comprised of one or more layers of conductive material. The conductive material selected for the plurality of conductive traces 225 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the plurality of conductive traces 225 have thermal expansion characteristics or a coefficient of thermal expansion (CTE) that is approximately equal to that of CTE of the supporting structure 220. Matching the CTE of components that contact one another is desirable because it eliminates the development of thermal stresses, which may occur during fabrication and the operation of the cable, and thus eliminates a known cause of mechanical failure in the components. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

As shown in FIG. 2, the lead assembly 200 may further comprise an electrode assembly 230. The electrode assembly 230 may be located at the distal end 215 of the lead assembly 200. In various embodiments, the electrode assembly 230 includes electrodes 240 and/or sensors formed on a supporting structure 245 using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In accordance with various aspects, the electrodes 240 may be provided as a high density electrode array comprising greater than sixteen electrodes. The supporting structure 245 may also provide support for microelectronic structures including a wiring layer 245 (e.g., one or more conductive traces) and optional via contact(s) (not shown). The wiring layer 245 may be embedded within or located on a surface of the supporting structure 245. The wiring layer 245 may be used to electrically connect directly or indirectly the electrodes 240 with one or more conductive traces of the plurality of conductive traces 225. The term "directly", as used herein, may be defined as being without something in between. The term "indirectly", as used herein, may be defined as having something in between. In some embodiments, the electrodes 240 make electrical contact with the wiring layer 245 by using via contact(s) there between.

In various embodiments, the supporting structure 220 of the cable 205 and the supporting structure 235 of the electrode assembly 230 are the same structure (i.e., the supporting structures 220, 235 are monolithic). Moreover, the one or more conductive traces of the plurality of conductive traces 225 and the wiring layer 245 may all be fabricated using the same layer of conductive material. In other words, the one or more conductive traces of the plurality of conductive traces 225 and the wiring layer 245 may be a continuous layer of conductive material (e.g., one or more layers of conductive material). In alternative embodiments, the supporting structure 220 of the cable 205 and the supporting structure 235 of the electrode assembly 230 are different structures but are connected such that there is an electrical connection between the one or more conductive traces of the plurality of conductive traces 225, the wiring layer 245, and the one or more electrodes 240.

As shown in FIG. 2, the lead assembly 200 may further comprise a multi-sectioned connector 250. The multi-sectioned connector 250 may be located at the proximal end 210 of the lead assembly 200. In various embodiments, the multi-sectioned connector 250 includes conductive contacts 255 formed in sections on one or more supporting structures 260 using various shapes and patterns to create certain types of contacts (e.g., bond pads, annular rings, split-annular rings, etc.). The supporting structures 260 may also provide support for microelectronic structures including a wiring layer 265 (e.g., one or more conductive traces) and optional via contact(s) (not shown). The wiring layer 265 may be embedded within or located on a surface of the supporting structure 260. The wiring layer 265 may be used to electrically connect directly or indirectly the conductive contacts 255 with one or more conductive traces of the plurality of conductive traces 225. In some embodiments, the conductive contacts 255 make electrical contact with the wiring layer 265 by using via contact(s) there between.

In various embodiments, the conductive contacts 255 and the wiring layer 265 are comprised of one or more layers of conductive material. The conductive material selected for the conductive contacts 255 and the wiring layer 265 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the conductive contacts 255 and the wiring layer 265 have thermal expansion characteristics or a coefficient of thermal expansion (CTE) that is approximately equal to that of CTE of the supporting structures 260. Matching the CTE of components that contact one another is desirable because it eliminates the development of thermal stresses, which may occur during fabrication and the operation of the cable, and thus eliminates a known cause of mechanical failure in the components.

In various embodiments, the supporting structure 220 of the cable 205 and the one or more supporting structures 260 of the multi-sectioned connector 250 are the same structure (i.e., the supporting structures 220, 260 are monolithic). Moreover, the one or more conductive traces of the plurality of conductive traces 225 and the wiring layer 265 may all be fabricated using the same layer of conductive material. In other words, the one or more conductive traces of the plurality of conductive traces 225 and the wiring layer 265 may be a continuous layer of conductive material (e.g., one or more layers of conductive material). In alternative embodiments, the supporting structure 220 of the cable 205 and the supporting structure 260 of the multi-sectioned connector 250 are different structures but are connected such that there is an electrical connection between the one or more conductive traces of the plurality of conductive traces 225, the wiring layer 265, and the conductive contacts 255.

As discussed herein, high density electrode arrays require many proximal contacts. This typically results in an excessively large connector to accommodate the space needed to present all of the proximal contacts as an electrical interface to the implantable neurostimulator. These excessively large connectors cannot be passed through cannulas used in typical deep brain implant techniques (e.g., a rigid metal trans-cranial precise stereotactic placement cannula) because of the maximum diameter of the lumen allowed for the cannulas to minimize trauma to the brain tissue. In order to overcome this problem and achieve additional advantages, the connectors of the present embodiments include multiple sections of conductive contacts that can be arranged in tandem to fit through the lumen of cannulas typically employed for deep brain implants, and subsequently re-arranged post implant such that the proximal contacts can be connected with a header of a neurostimulator.

Figure 3A:
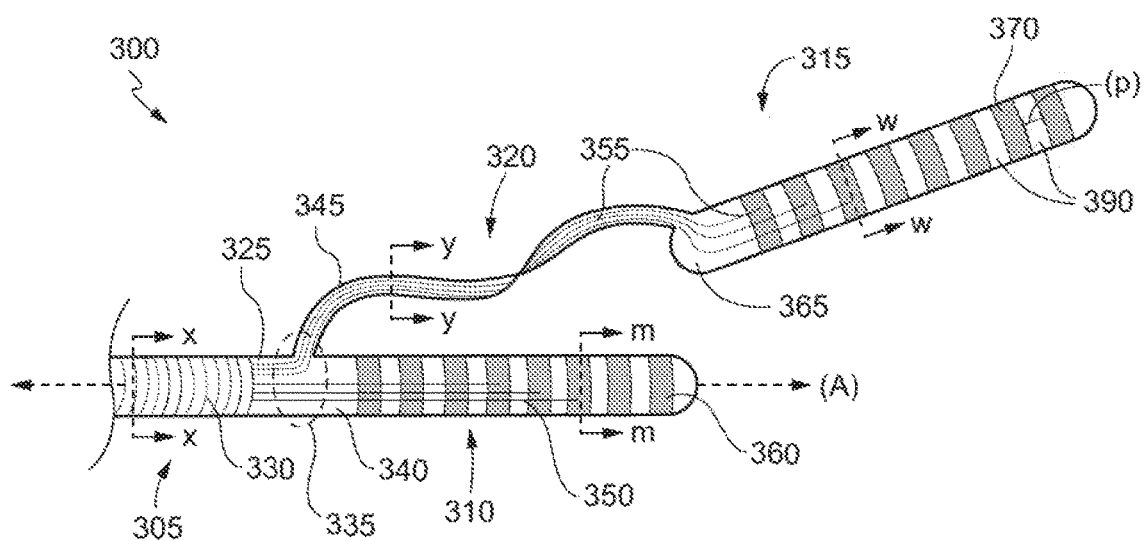
FIGS. 3A-3E show multi-sectioned connectors in accordance with various embodiments.
Figure 3B:
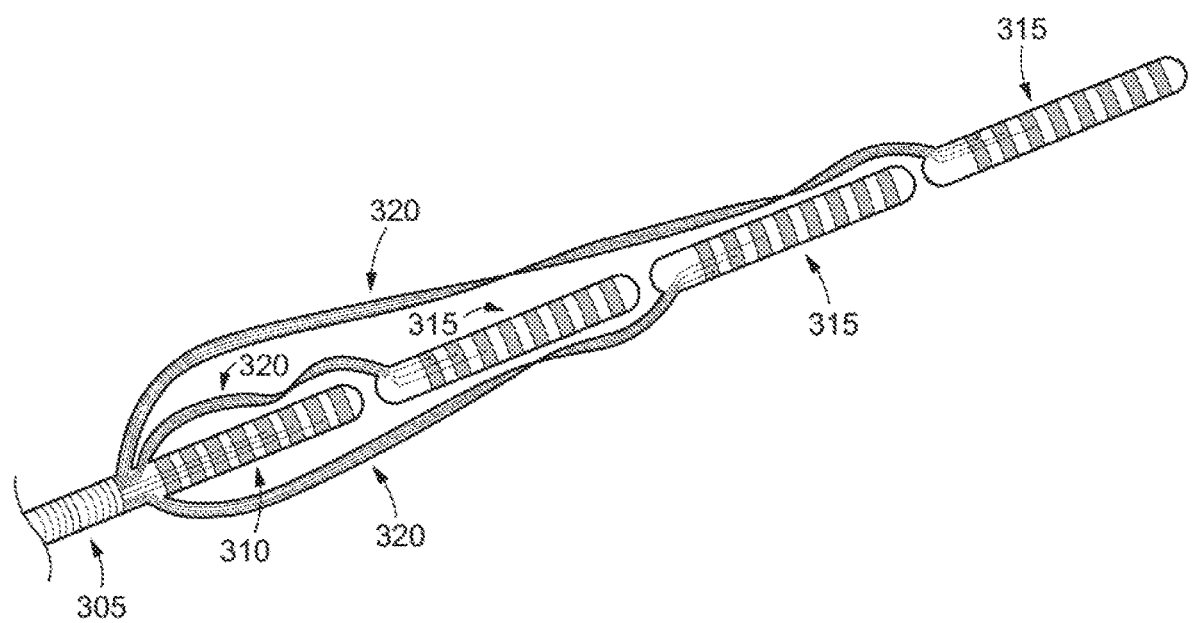

As shown in FIG. 3A, a multi-sectioned connector 300 (e.g., the multi-sectioned connector 250 discussed with respect to FIG. 2) may include a main body 305, a first section 310 (a first or primary plug) extending from the main body 305, and a second section 315 (a second or secondary plug) connected with the main body 305 via a flexible portion or bridge 320. Although FIG. 3A only shows a multi-sectioned connector arrangement having a main body, a primary section, a single secondary section, and a single flexible bridge connecting the secondary section to the main body, it should be understood that more than a single secondary section and more than a single flexible bridge may be implemented to provide various arrangements for connectors. For example, FIG. 3B shows a connector arrangement that includes a main body 305, a primary section 310, three secondary sections 315, and three flexible bridges 320 connecting the three secondary sections 315, respectively, to the main body 305.

The main body 305 may be a portion of the cable of the lead assembly located at the proximal end of the cable or a separate structure extending from the proximal end of the cable of the lead assembly. In either instance, the main body 305 comprises a supporting structure 325 (a first supporting structure) and a plurality of conductive traces 330 formed on a portion of the supporting structure 325. In some embodiments, the supporting structure 325 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 325 is made of one or more layers of dielectric material formed on a substrate. The substrate may be made from any type of metallic or non-metallic material.

In various embodiments, the plurality of conductive traces 330 are comprised of one or more layers of conductive material. The conductive material selected for the plurality of conductive traces 330 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the plurality of conductive traces 330 have thermal expansion characteristics or a coefficient of thermal expansion (CTE) that is approximately equal to that of CTE of the supporting structure 325. Matching the CTE of components that contact one another is desirable because it eliminates the development of thermal stresses, which may occur during fabrication and the operation of the connector, and thus eliminates a known cause of mechanical failure in the components.

At one or more locations or regions 335 along the longitudinal axis (A) of the main body 305, one or more layers of the supporting structure 325 bifurcate to form a supporting structure 340 (e.g., a second supporting structure) of the first section 310 and a supporting structure 345 (e.g., a third supporting structure) of the flexible portion or bridge 320. Additionally at the one or more locations or regions 335, some traces of the plurality of conductive traces 330, for example, a first set of conducive traces 350 from the plurality of traces 330 continue (lengthen or are formed) along the supporting structure 340 (e.g., a second supporting structure) of the first section 310; whereas some other traces of the plurality of conductive traces 330, for example, a second set of conducive traces 355 from the plurality of traces 330 continue (lengthen or are formed) along the supporting structure 345 (e.g., a third supporting structure) of the flexible portion or bridge 320. The first set of conducive traces 350 electrically connect with a plurality of conductive contacts 360 (e.g., a first set of conductive contacts) formed on a surface of the supporting structure 340. The supporting structure 345 (e.g., a third supporting structure) of the flexible portion or bridge 320 extends to form a supporting structure 365 (e.g., a fourth supporting structure) of the second section 315. The second set of conducive traces 355 continue (lengthen or are formed) along the supporting structure 365 (e.g., a fourth supporting structure) and electrically connect with a plurality of conductive contacts 370 (e.g., a second set of conductive contacts) formed on a surface of the supporting structure 365.

At least one trace from the set of conductive traces 350 terminates at a conductive contact 360 exposed on a surface of the supporting structure 340. Alternatively, each trace from the set of conductive traces 350 terminates at a conductive contact 360 exposed on a surface of the supporting structure 340. At least one trace from the set of conductive traces 355 terminates at a conductive contact 370 exposed on a surface of the supporting structure 365. Alternatively, each trace from the set of conductive traces 355 terminates at a conductive contact 370 exposed on a surface of the supporting structure 365. As should be understood, in some embodiments, each electrode from the electrode assembly is electrically connected via optional via contacts, wiring layers, and conductive traces to a respective conductive contact. In other words, each electrode may be electrically connected to a different conductive contact (a one to one relationship). In alternative embodiments, a multiplexer chip may be used such that sets of electrodes (multiple electrodes) from the electrode assembly are electrically connected via optional via contacts, wiring layers, and conductive traces to a respective conductive contact. In other words, each electrode may be electrically connected to a same or different conductive contact (a many to one relationship).

The plurality of conductive traces 330 and the sets of conductive traces 350, 355 may be deposited onto a surface of the supporting structures 325, 340, 345, 365 by using thin film deposition techniques well known to those skilled in the art such as by sputter deposition, chemical vapor deposition, metal organic chemical vapor deposition, electroplating, electroless plating, and the like. In some embodiments, the thickness of the plurality of conductive traces 330 and sets of conductive traces 350, 355 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structures 325, 340, 345, 365. If, however, a signal plane having a relatively low impedance is desired, a greater thickness of electrically conductive material should be deposited onto the supporting structures 325, 340, 345, 365. In certain embodiments, each of plurality of conductive traces 330 and sets of conductive traces 350, 355 has a thickness (t). In some embodiments, the thickness (t) is from 0.5 µm to 25 µm or from 5 µm to 10 µm, for example about 5 µm or about 8 µm. In some embodiments, each of plurality of conductive traces 330 and sets of conductive traces 350, 355 has a length (l) of about 1 mm to 100 mm or 1 cm to 3 cm, e.g., about 15 mm. In some embodiments, each of the plurality of conductive traces 330 and sets of conductive traces 350, 355 has a width (w) from 2.0 µm to 500 µm, for example about 30 µm or about 50 µm.

Figure 3C:
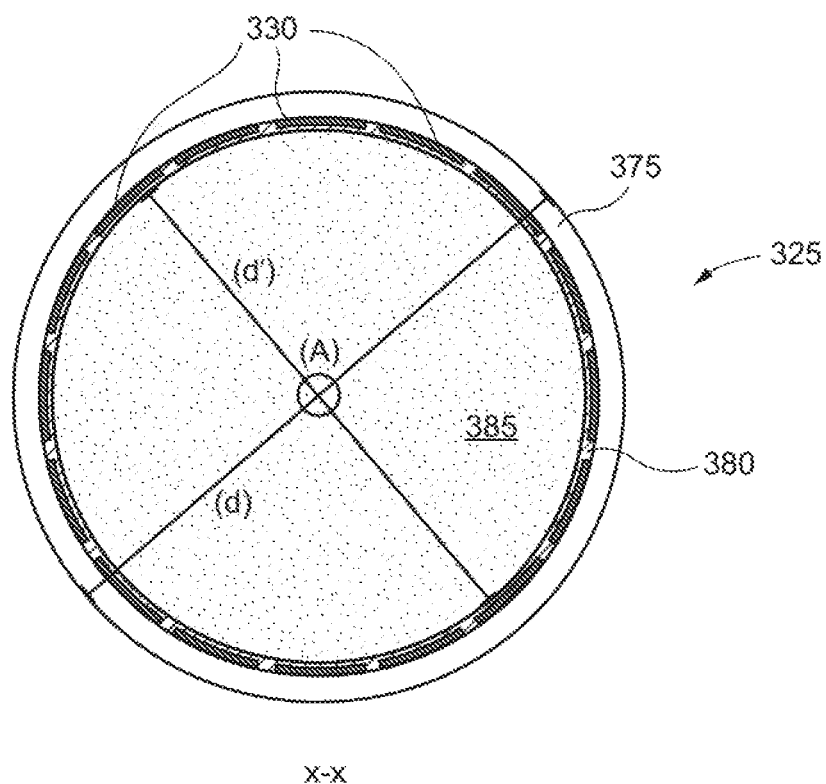

As shown in FIG. 3C (cross-section of the main body 305 along X-X from FIG. 3A), the supporting structure 325 may comprise a first layer of dielectric material 375 and a second layer of dielectric material 380 with the plurality of conductive traces 330 buried between the first layer of dielectric material 375 and the second layer of dielectric material 380. The dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The first layer of dielectric material 375 may be comprised of the same material or a different material from that of the second layer of dielectric material 380. For example, the first layer of dielectric material 375 may be a high temperature liquid crystal polymer, and the second layer of dielectric material 380 may be a low temperature liquid crystal polymer. As used herein, "a high temperature liquid crystal polymer" refers to a liquid crystal polymer with a high melting temperature of greater than 300° C. As used herein, "a low temperature liquid crystal polymer" refers to a liquid crystal polymer with a low melting temperature of less than 300° C.

As illustrated in FIG. 3C, the main body 305 may be a cylindrical tube. As used herein, "cylindrical" means having straight parallel sides and a circular or oval cross-section; in the shape or form of a cylinder. Although the main body 305 is described herein with respect to a cylindrical tube shape, it should be understood that other shapes for the main body 305 have been contemplated, for example, flat (planar), cubed, spherical cubed, torus, ellipsoid, etc. In some embodiments, the cylindrical tube is fabricated with at least the layers of dielectric material 375, 380. For example, the one or more layers of dielectric material 375, 380 may be wrapped in a longitudinal manner around the longitudinal axis (A) or wrapped in a helical manner around the longitudinal axis (A). The first layer of dielectric material 375 may define an outer diameter (d) of the cylindrical tube and the second layer of dielectric material 380 may define an inner diameter (d') of the cylindrical tube. The cylindrical tube may be further fabricated to include a lumen 385 defined by the inner diameter (d'). The lumen 385 may be hollow or may be at least partially filled with one or more layers of material to create a core with a hardness measured by a Shore A durometer of greater than 70 A. In some embodiments, the one or more layers of material of the core are polyimide, liquid crystal polymer, parylene, polyether ether ketone, polyurethane, metal, or a combination thereof. In certain embodiments, the one or more layers of material of the core are a thermosetting or thermoplastic polyurethane.

Figure 3D:
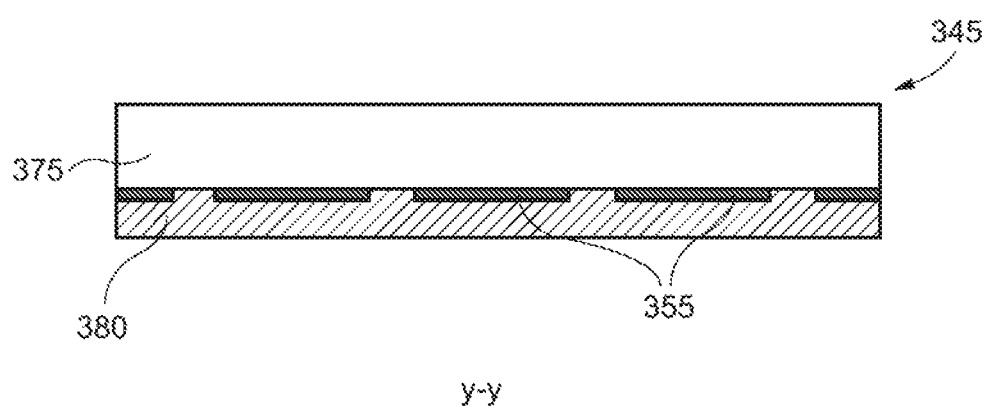

As shown in FIG. 3D (cross-section of a flexible portion or bridge 320 along Y-Y from FIG. 3A), the supporting structure 345 may comprise the first layer of dielectric material 375 and the second layer of dielectric material 380 with the set of conductive traces 355 buried between the first layer of dielectric material 375 and the second layer of dielectric material 380. For example, the supporting structure 325 may bifurcate and be extended to form the supporting structure 345. As with the supporting structure 325, the first layer of dielectric material 375 may be comprised of the same material or a different material from that of the second layer of dielectric material 380. For example, the first layer of dielectric material 375 may be a high temperature liquid crystal polymer, and the second layer of dielectric material 380 may be a low temperature liquid crystal polymer. As illustrated in FIG. 3D, the flexible portion or bridge 320 may be a flat (planar) or ribbon shaped structure. Although the flexible portion or bridge 320 is described herein with respect to a flat (planar) or ribbon shape, it should be understood that other shapes for the flexible portion or bridge 320 have been contemplated, for example, cylindrical, cubed, spherical cubed, torus, ellipsoid, etc. In some embodiments, the flat (planar) or ribbon shaped structure is fabricated from at least the layers of dielectric material 375, 380.

Figure 3E:
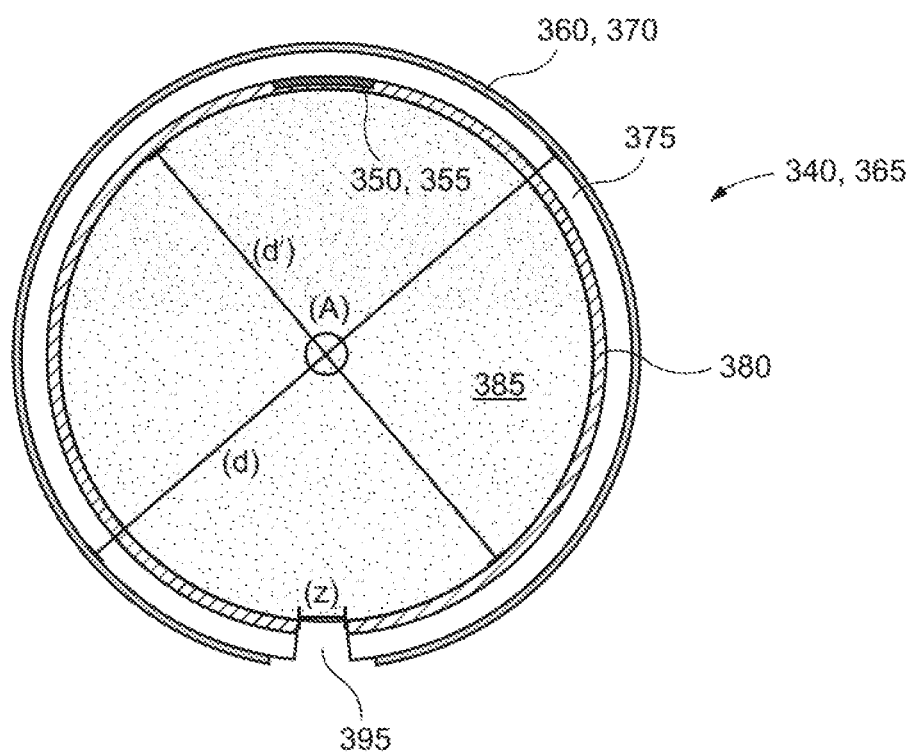

As shown in FIG. 3E (cross-section of the first section 310 along M-M or the second section 315 along W-W from FIG. 3A), the supporting structure 340, 365 may comprise the first layer of dielectric material 375 and the second layer of dielectric material 380 with a set of conductive traces 355 buried between the first layer of dielectric material 375 and the second layer of dielectric material 380. For example, the supporting structure 325 may bifurcate and be extended to form the supporting structure 340 and/or the supporting structure 345 may be extended to form the supporting structure 365. As with the supporting structure 325 and the supporting structure 345, the dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The first layer of dielectric material 375 may be comprised of the same material or a different material from that of the second layer of dielectric material 380. For example, the first layer of dielectric material 375 may be a high temperature liquid crystal polymer, and the second layer of dielectric material 380 may be a low temperature liquid crystal polymer.

As illustrated in FIG. 3E, the first section 310 and the second section 315 may be a cylindrical tube. Although the first section 310 and the second section 315 are described herein with respect to a cylindrical tube shape, it should be understood that other shapes for the first section 310 and the second section 315 have been contemplated, for example, flat (planar), cubed, spherical cubed, torus, ellipsoid, etc. In some embodiments, the cylindrical tube is fabricated with at least the layers of dielectric material 375, 380. For example, the one or more layers of dielectric material 375, 380 may be wrapped in a longitudinal manner around the longitudinal axis (A) or wrapped in a helical manner around the longitudinal axis (A). In some embodiments, the one or more layers of dielectric material 375, 380 are at least partially wrapped around the lumen 385. For example, the one or more layers of dielectric material 375, 380 may be formed as a split cylindrical tube wrapped around the lumen 385, and the split cylindrical tube comprises a gap 395 for the split having a predefined width (z). The predefined width may be between 0.1 mm and 10 mm, for example about 1 mm.

The first layer of dielectric material 375 may define an outer diameter (d) of the cylindrical tube and the second layer of dielectric material 380 may define an inner diameter (d') of the cylindrical tube. The cylindrical tube may be further fabricated to include the lumen 385 defined by the inner diameter (d'). The lumen 385 may be hollow or may be at least partially filled with one or more layers of material to create a core with hardness measured by a Shore A durometer of greater than 70 A. In some embodiments, the one or more layers of material of the core are polyimide, liquid crystal polymer, parylene, polyether ether ketone, polyurethane, metal, or a combination thereof. In certain embodiments, the one or more layers of material of the core are a thermosetting or thermoplastic polyurethane.

In some embodiments, the conductive contacts 360, 370 are annular rings positioned around the longitudinal axis (A) of the cylindrical tube and exposed on the surface of the cylindrical tube. Each annular ring may be spaced apart from one another on the surface of the cylindrical tube by a region 390 (shown in FIG. 3A) of the first layer of the dielectric material 375. A width (p) of the region 390 of the first layer of the dielectric material 375 that separates each split annular ring may be between 0.1 mm to 6 mm, for example about 0.4 mm. In some embodiments, each annular ring connects to a single trace from the first or second set of conductive traces 350, 355. In other embodiments, each annular ring connects to two or more traces from the first or second set of conductive traces 350, 355. For example, the annular rings may be split and a left side of the split annular ring may be connected with a first trace and a right side of the annular ring may be connected with a second trace. Alternatively, a multiplexer chip may be used to drive signals and thus the annular ring may be connected to multiple traces from the first or second set of conductive traces 350, 355. In various embodiments, eight conductive contacts 360, 370 or annular rings are positioned around the longitudinal axis (A) of each cylindrical tube and exposed on the surface of each cylindrical tube; however, it should be understood that more or less than eight conductive contacts 360, 370 or annular rings can be positioned on the cylindrical tubes. For example, each cylindrical tube can have the same or a different amount of the conductive contacts 360, 370 or split annular rings (1, 2, 3, 4, 5, 6, 7, 8, 9, 10, 11, etc.) to enhance design flexibility for the connector 300.

Figure 4A:
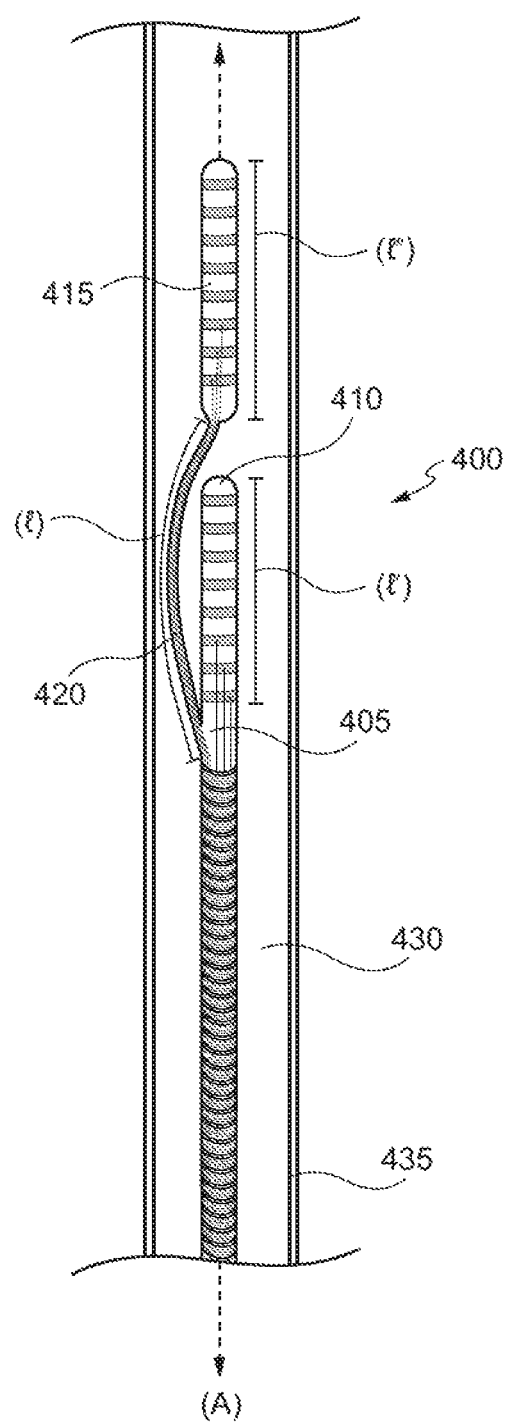
FIGS. 4A-4C show multi-sectioned connectors in various arrangements in accordance with various embodiments.

FIG. 4A shows a connector 400 (e.g., the connector 300 described with respect to FIGS. 3A-3E) comprising a main body 405, a first section 410 (primary section), and a second section 415 (secondary section) connected via a flexible portion or bridge 420 to the main body 405. The connector 400 may be arranged linearly with the main body 405, the first section 410, and the second section 415 arranged in tandem aligned along the longitudinal axis (A) of the main body 405. This arrangement allows a lead assembly with the connector 400 to pass completely through the lumen 430 of a rigid cannula 435, as the main body 405, the first section 410, and the second section 415 are capable of lining up like train cars on a track as the connector 400 passes through the cannula 435 during implant. In order for the main body 405, the first section 410, and the second section 415 to line up linearly, the flexible portion or bridge 420 is structured to enable the second section 415 to extend beyond the first section 410 and align along the longitudinal axis (A) of the main body 405. In various embodiments, structured means that the flexible portion or bridge 420 has (i) a predetermined degree of flexibility, and/or (ii) a predetermined length (l) that allows the second section 415 to extend beyond the first section and align along the longitudinal axis (A) of the main body 405.

In some embodiments, the flexibility of the flexible portion or bridge 420 allows for the flexible portion or bridge 420 to be positioned along a side of the first section 410 (disposed out of alignment with the main body 405, the first section 410, and the second section 415) in an unobtrusive manner such that the connector 400 can pass through lumen 430. The flexibility of the flexible portion or bridge 420 may be characterized by its hardness and/or elongation of break. The elongation of break is the ratio between increased length and initial length after breakage of the tested specimen at a controlled temperature. In some embodiments, the flexible portion or bridge 420 has a hardness measured by a Shore A durometer of less than 95 A. In some embodiments, the flexible portion or bridge 420 has a hardness measured by a Shore A durometer of equal to or less than 70 A. In certain embodiments, the flexible portion or bridge 420 has a hardness, measured by a Shore A durometer, that is less than the hardness, measured by a Shore A durometer, of the first section 405 and/or the second section 415. In some embodiments, the flexible portion or bridge 420 has an elongation of break of at least 10%. In some embodiments, the flexible portion or bridge 420 has an elongation of break of greater than 100%, up to and including 1000%. In certain embodiments, the elongation of break of the flexible portion or bridge 420 is greater than the elongation of break of the first section 405 and/or the second section 415.

In some embodiments, the length (l) of the flexible portion or bridge 420 allows for the second portion 415 to be positioned in front of or in tandem with the first section 410 (disposed in alignment with the main body 405 and the first section 410) in an unobtrusive manner such that the connector 400 can pass through lumen 430. In certain embodiments, the length (l) of the flexible portion or bridge 420 is greater than a length (l') of at least the first section 410. As should be understood, the length (l) of a flexible portion or bridge 420 may need to be even greater than (l') of the first section 405 when there are more than one secondary sections. For example, if a third section (a second secondary section is included with the connector as shown in FIG. 3B), then the length (l) of the flexible portion or bridge 420 connected with the third section would need to be greater than at least the length (l') of the first section and the length (l") of the second section 410 in order for the main body 405, the first section 410, the second section 415, and the third section to line up linearly.

Figure 4B:
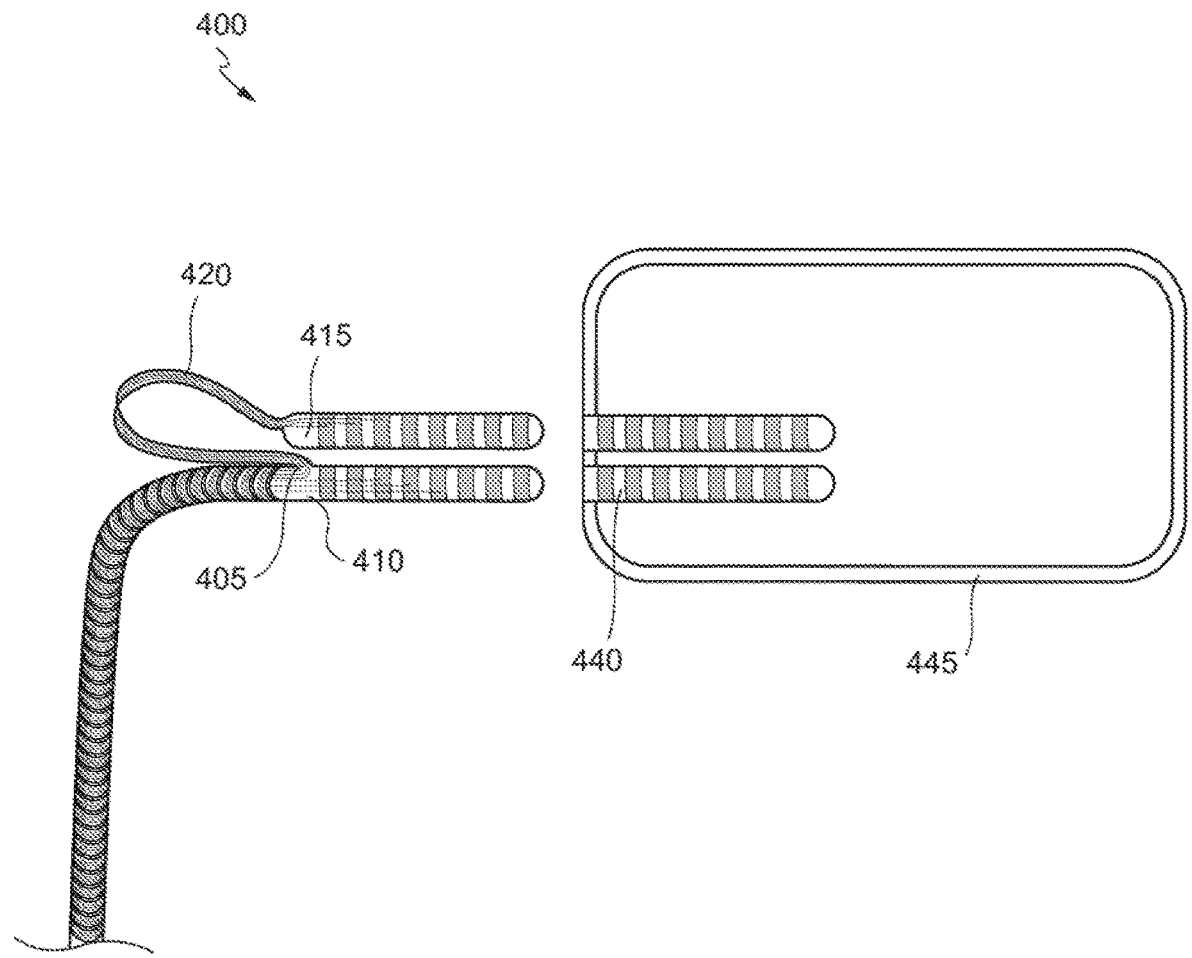

FIG. 4B shows the connector 400 may be arranged spread out with the second section 415 disposed in a rational or arbitrary position relative to the first section 410. In some embodiments, prior to insertion of the connector 400 into header 440 of an implantable neurostimulator 445, the first section 410 and the second section 415 may be brought into a rational arrangement with one another, e.g., parallel to one another, as shown in FIG. 4B. This arrangement allows the first section 410 and the second section 415 to be aligned and connected with a typical header of an implantable neurostimulator. However, a rational arrangement may not be necessary for connection in many circumstances. In some embodiments, because of the length (l) of the flexible portion or bridge 420, prior to insertion of the connector 400 into header 440 of an implantable neurostimulator, the first section 410 and the second section 415 may be displaced in an arbitrary arrangement with one another and subsequently connected with the header 440 of the implantable neurostimulator 445.

Figure 4C:
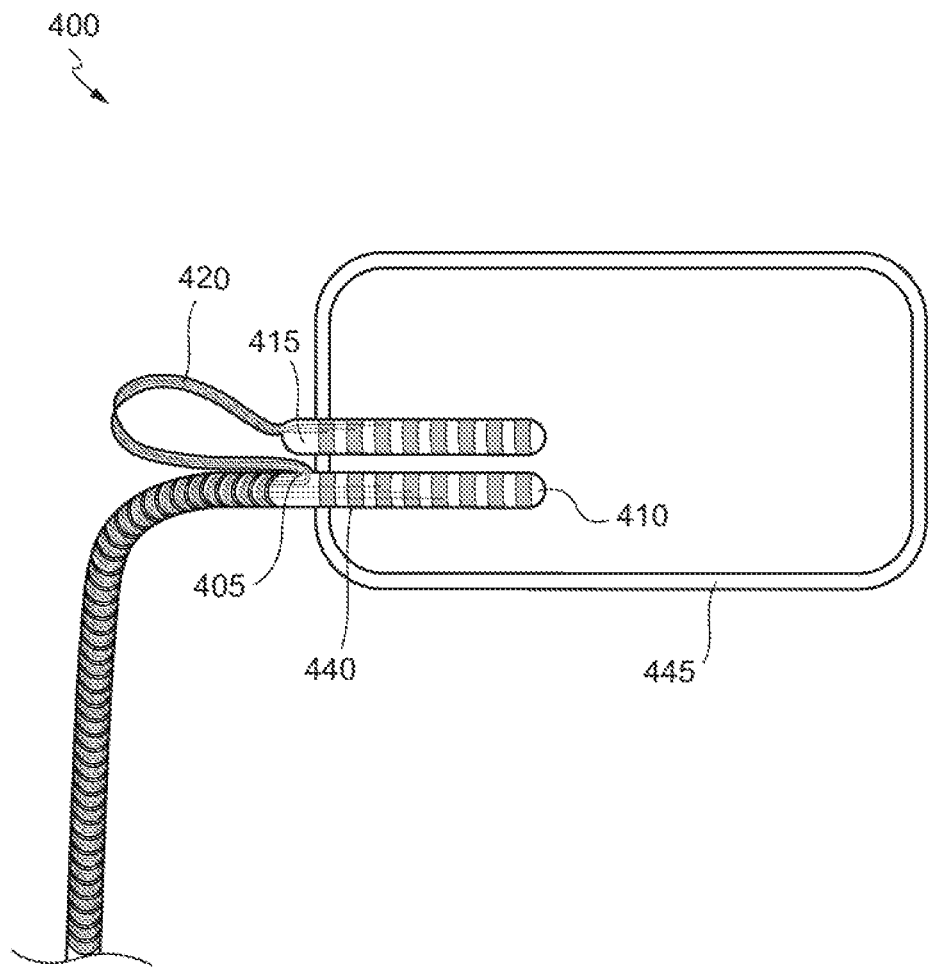

FIG. 4C shows the first section 410 and the second section 415 inserted into the header 440 such that the conductive contacts on the first section 410 and the second section 415 make electrical connection with respective conductive contacts within the header 440 (this ultimately connects the electrodes with the electronics module of the implantable neurostimulator 445). As shown, upon connection, in some embodiments, the flexible portion or bridge 420 remains external to the header 440.

Figure 5A:
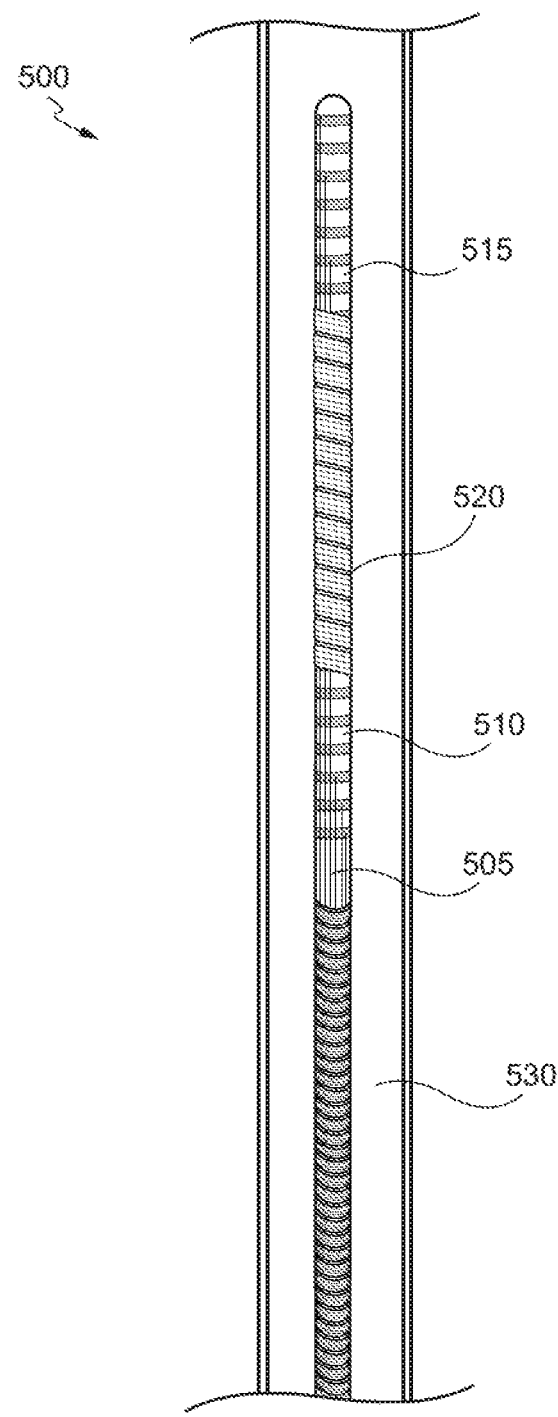
FIGS. 5A-5E show alternative multi-sectioned connectors in accordance with various embodiments.

FIG. 5A shows a connector 500 (e.g., the connector 300 described with respect to FIGS. 3A-3E) comprising a main body 505, a first section 510 (a first or primary plug), and a second section 515 (a second or secondary plug) connected via a flexible portion or bridge 520 to the main body 505. In some embodiments, a stylet 525 is provided to add stiffness to the lead assembly and connector during implantation. As described with respect to FIGS. 4A-4C, the connector 500 may be arranged linearly with the main body 505, the first section 510, and the second section 515 arranged in tandem aligned along the longitudinal axis (A) of the main body 505. However, in some embodiments, the flexible portion or bridge 520 is provided as a helical flexible portion or bridge 520. This arrangement allows a lead assembly with the connector 500 to pass completely through the lumen 530 of a rigid cannula 535, as the main body 505, the first section 510, and the second section 515 are capable of lining up like train cars on a track as the connector 500 passes through the cannula 535 during implant. In order for the main body 505, the first section 510, and the second section 515 to line up linearly, the helical flexible portion or bridge 520 is structured to enable the second section 515 to extend beyond the first section 510 and align along the longitudinal axis (A) of the main body 505. In various embodiments, structured means that the flexible portion or bridge 520 has (i) a predetermined degree of flexibility, and/or (ii) a predetermined length (l) and helical turns (t) that allows the second section 515 to extend beyond the first section and align along the longitudinal axis (A) of the main body 505.

In some embodiments, the helical flexibility of the helical flexible portion or bridge 520 allows for the helical flexible portion or bridge 520 to be wrapped around the first section 510 (disposed in alignment with the main body 505, the first section 510, and the second section 515) in an unobtrusive manner such that the connector 500 can pass through lumen 530. As described with respect to FIGS. 4A-4C, the flexibility of the helical flexible portion or bridge 520 may be characterized by its hardness and/or elongation of break In some embodiments, the helical flexible portion or bridge 520 has a hardness measured by a Shore A durometer of less than 95 A. In some embodiments, the helical flexible portion or bridge 520 has a hardness measured by a Shore A durometer of equal to or less than 70 A. In certain embodiments, the helical flexible portion or bridge 520 has a hardness, measured by a Shore A durometer, that is less than the hardness, measured by a Shore A durometer, of the first section 505 and/or the second section 515. In some embodiments, the helical flexible portion or bridge 520 has an elongation of break of at least 10%. In some embodiments, the helical flexible portion or bridge 520 has an elongation of break of greater than 100%, up to and including 1000%. In certain embodiments, the elongation of break of the helical flexible portion or bridge 520 is greater than the elongation of break of the first section 505 and/or the second section 515

Moreover, the length (l) and number of helical turns (t) of the flexible portion or bridge 520 allows for the second portion 515 to be positioned in front of or in tandem with the first section 510 (disposed in alignment with the main body 505 and the first section 510) in an unobtrusive manner such that the connector 500 can pass through lumen 530. In certain embodiments, the length (l) of the helical flexible portion or bridge 520 is greater than a length (l') of at least the first section 510. As should be understood, the length (l) of a helical flexible portion or bridge 520 may need to be even greater than (l') of the first section 505 when there are more than one secondary sections.

Figure 5B:
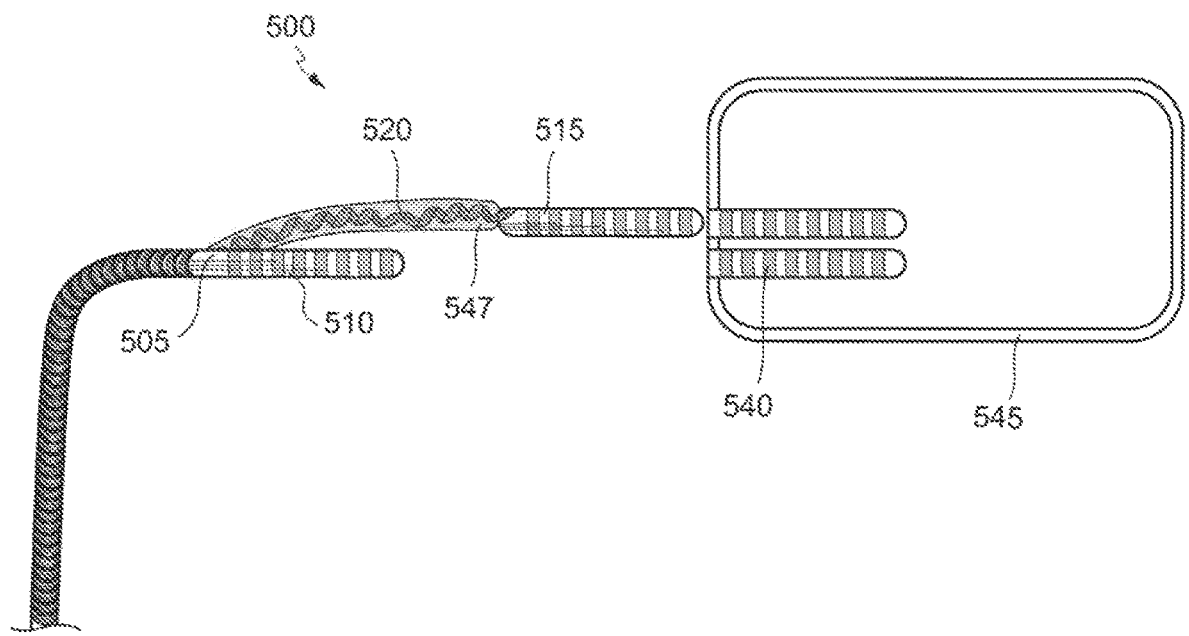

FIG. 5B shows the connector 500 may be arranged spread out with the second section 515 disposed in a rational or arbitrary position relative to the first section 510. For example, after implantation of the lead assembly with the connector 400, withdrawal of the cannula 535, and removal of the stylet 525, the helical flexible portion or bridge 520 is unwound from the first section 510 to separate the first section 510 and the second section 515. In some embodiments, prior to insertion of the connector 500 into header 540 of an implantable neurostimulator 545, the first section 510 and the second section 515 may be brought into a rational arrangement with one another, e.g., parallel to one another, as shown in FIG. 5B. This arrangement allows the first section 510 and the second section 515 to be aligned and connected with a typical header of an implantable neurostimulator. However, a rational arrangement may not be necessary for connection in many circumstances. In some embodiments, because of the length (l) of the helical flexible portion or bridge 520, prior to insertion of the connector 500 into header 540 of an implantable neurostimulator 545, the first section 510 and the second section 515 may be displaced in an arbitrary arrangement with one another and subsequently connected with the header 540 of the implantable neurostimulator 545. In some embodiments, after the helical flexible portion or bridge 520 is unwound from the first section 510, a silicone sleeve 547 is placed over the helical flexible portion or bridge 520 to protect the helical flexible portion or bridge 520 while implanted in a body.

Figure 5C:
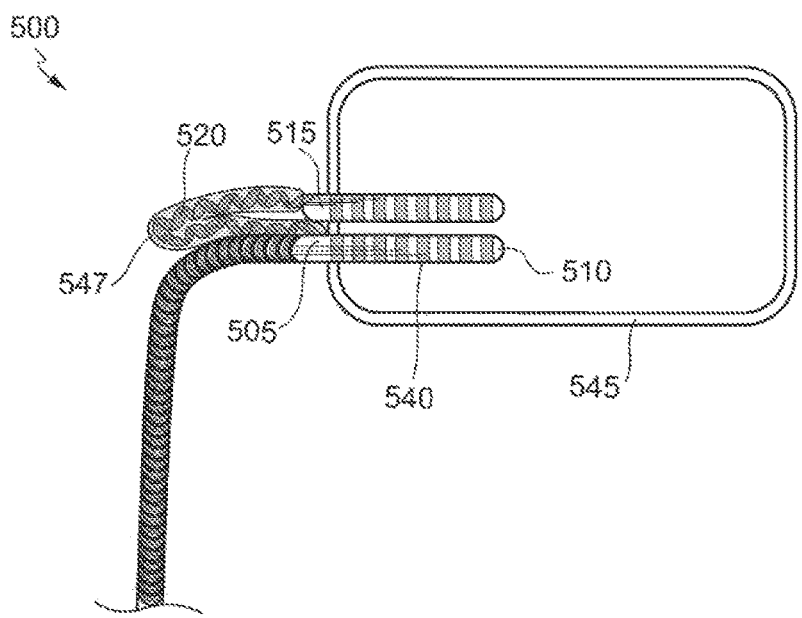

FIG. 5C shows the first section 510 and the second section 515 inserted into the header 540 such that the conductive contacts on the first section 510 and the second section 515 make electrical connection with respective conductive contacts within the header 540 (this ultimately connects the electrodes with the electronics module of the implantable neurostimulator 545). As shown, upon connection, in some embodiments, the helical flexible portion or bridge 520 remains external to the header 540.

Figure 5D:
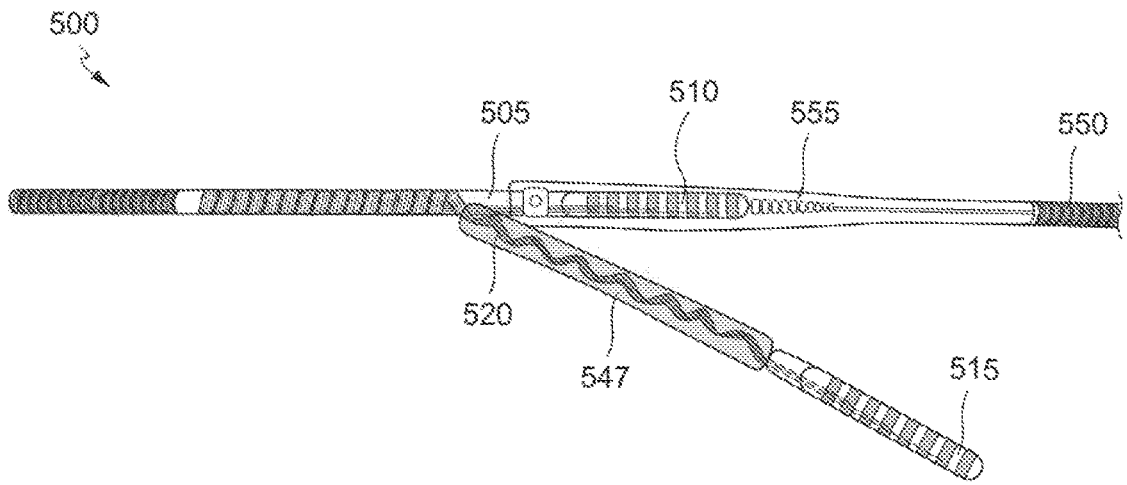
Figure 5E:
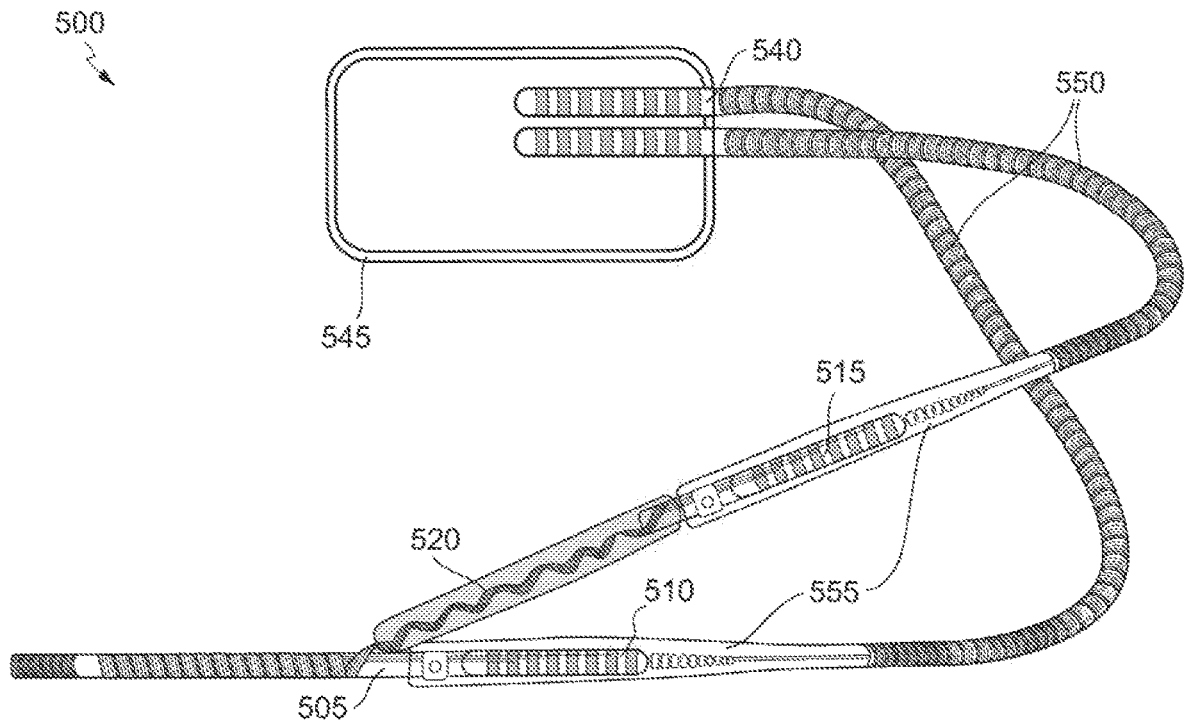

FIG. 5D shows the first section 510 and the second section 515 may be inserted into lead extenders 550 rather than directly into the header 540. The conductive contacts on the first section 510 and the second section 515 make electrical connection with respective conductive contacts within connectors 555 of the extenders 550. As shown in FIG. 5E, the extenders 550 may be connected with the header 540 (this ultimately connects the electrodes with the electronics module of the implantable neurostimulator 545).

Figure 6A:
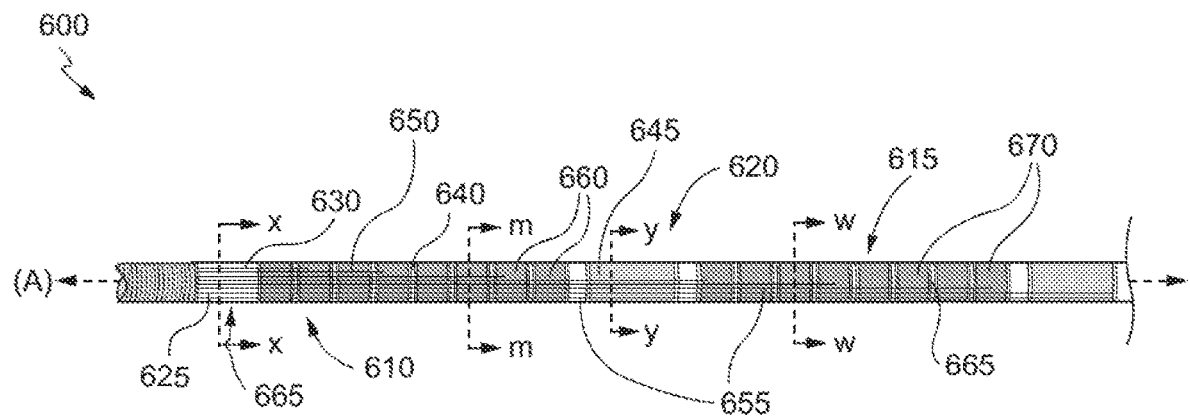
FIGS. 6A-6E show alternative multi-sectioned connectors in accordance with various embodiments.
Figure 6B:
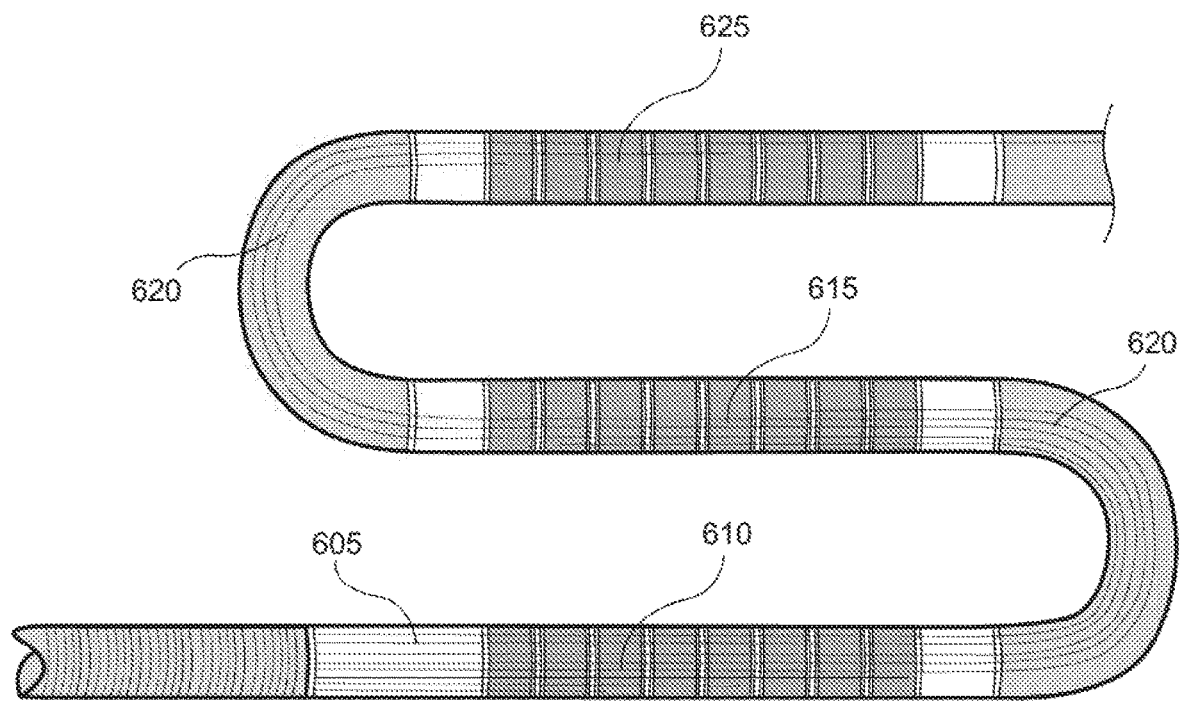

As shown in FIG. 6A, an alternative multi-sectioned connector 600 (e.g., the multi-sectioned connector 250 discussed with respect to FIG. 2) may include a main body 605, a first section 610 (a first or primary plug) extending from the main body 605, and a second section 615 (a second or secondary plug) connected with the first section 610 via a flexible portion or bridge 620. Although FIG. 6A only shows a multi-sectioned connector arrangement having a main body, a primary section, a single secondary section, and a single flexible bridge connecting the secondary section to the primary section, it should be understood that more than a single secondary section and more than a single flexible bridge may be implemented to provide various arrangements for connectors. For example, FIG. 6B shows a connector arrangement that includes a main body 605, a primary section 610, two secondary sections 615, and two flexible bridges 620 connecting the two secondary sections 615, respectively, to the primary section 610 and the prior secondary sections 615.

The main body 605 may be a portion of the cable of the lead assembly located at the proximal end of the cable or a separate structure extending from the proximal end of the cable of the lead assembly. In either instance, the main body 605 comprises a supporting structure 625 (a first supporting structure) and a plurality of conductive traces 630 formed on a portion of the supporting structure 625. In some embodiments, the supporting structure 625 is made of one or more layers of dielectric material (i.e., an insulator). The dielectric material may be selected from the group of electrically flexible nonconductive materials consisting of organic or inorganic polymers, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In other embodiments, the supporting structure 625 is made of one or more layers of dielectric material formed on a substrate. The substrate may be made from any type of metallic or non-metallic material.

In various embodiments, the plurality of conductive traces 630 are comprised of one or more layers of conductive material. The conductive material selected for the plurality of conductive traces 630 should have good electrical conductivity and may include pure metals, metal alloys, combinations of metals and dielectrics, and the like. For example, the conductive material may be platinum (Pt), platinum/iridium (Pt/Ir), titanium (Ti), gold/titanium (Au/Ti), or any alloy thereof. In some embodiments, it is also desirable that the conductive material selected for the plurality of conductive traces 630 have thermal expansion characteristics or a coefficient of thermal expansion (CTE) that is approximately equal to that of CTE of the supporting structure 625. Matching the CTE of components that contact one another is desirable because it eliminates the development of thermal stresses, which may occur during fabrication and the operation of the connector, and thus eliminates a known cause of mechanical failure in the components.

Along the longitudinal axis (A) of the main body 605, one or more layers of the supporting structure 625 extend to form a supporting structure 640 (e.g., a second supporting structure) of the first section 610. Additionally at least some traces of the plurality of conductive traces 630, for example, a first set of conductive traces 650 from the plurality of traces 630 continue (lengthen or are formed) along the supporting structure 640 (e.g., a second supporting structure) of the first section 610. The first set of conductive traces 650 electrically connect with a plurality of conductive contacts 660 (e.g., a first set of conductive contacts) formed on a surface of the supporting structure 640. Some other traces of the plurality of conductive traces 630, for example, a second set of conductive traces 655 from the plurality of traces 630 continue (lengthen or are formed) along the supporting structure 640 (e.g., a second supporting structure) of the first section 610.

Along the longitudinal axis (A) of the main body 605, one or more layers of the supporting structure 640 extend to form a supporting structure 645 (e.g., a third supporting structure) of the flexible portion or bridge 620. Additionally at least some traces of the plurality of conductive traces 630, for example, the second set of conductive traces 655 from the plurality of traces 630 continue (lengthen or are formed) along the supporting structure 645 (e.g., a third supporting structure) of the flexible portion or bridge 620. The supporting structure 645 (e.g., a third supporting structure) of the flexible portion or bridge 620 extends to form a supporting structure 665 (e.g., a fourth supporting structure) of the second section 615. The second set of conductive traces 655 continue (lengthen or are formed) along the supporting structure 665 (e.g., a fourth supporting structure) and electrically connect with a plurality of conductive contacts 670 (e.g., a second set of conductive contacts) formed on a surface of the supporting structure 665.

At least one trace from the set of conductive traces 650 terminates at a conductive contact 660 exposed on a surface of the supporting structure 640. Alternatively, each trace from the set of conductive traces 650 terminates at a conductive contact 660 exposed on a surface of the supporting structure 640. At least one trace from the set of conductive traces 655 terminates at a conductive contact 670 exposed on a surface of the supporting structure 665. Alternatively, each trace from the set of conductive traces 655 terminates at a conductive contact 670 exposed on a surface of the supporting structure 665. As should be understood, in some embodiments, each electrode from the electrode assembly is electrically connected via optional via contacts, wiring layers, and conductive traces to a respective conductive contact. In other words, each electrode may be electrically connected to a different conductive contact (a one to one relationship). In alternative embodiments, a multiplexer chip may be used such that sets of electrodes (multiple electrodes) from the electrode assembly are electrically connected via optional via contacts, wiring layers, and conductive traces to a respective conductive contact. In other words, each electrode may be electrically connected to a same or different conductive contact (a many to one relationship).

The plurality of conductive traces 630 and the sets of conductive traces 650, 655 may be deposited onto a surface of the supporting structures 625, 640, 645, 665 by using thin film deposition techniques well known to those skilled in the art such as by sputter deposition, chemical vapor deposition, metal organic chemical vapor deposition, electroplating, electroless plating, and the like. In some embodiments, the thickness of the plurality of conductive traces 630 and sets of conductive traces 650, 655 is dependent on the particular impedance desired for conductor, in order to ensure excellent signal integrity (e.g., electrical signal integrity for stimulation or recording). For example, if a conductor having a relatively high impedance is desired, a small thickness of conductive material should be deposited onto the supporting structures 625, 640, 645, 665. If, however, a signal plane having a relatively low impedance is desired, a greater thickness of electrically conductive material should be deposited onto the supporting structures 625, 640, 645, 665. In certain embodiments, each of plurality of conductive traces 630 and sets of conductive traces 650, 655 has a thickness (t). In some embodiments, the thickness (t) is from 0.5 μm to 25 μm or from 5 μm to 10 μm, for example about 5 μm or about 8 μm. In some embodiments, each of plurality of conductive traces 630 and sets of conductive traces 650, 655 has a length (l) of about 1 mm to 100 mm or 1 cm to 3 cm, e.g., about 15 mm. In some embodiments, each of the plurality of conductive traces 630 and sets of conductive traces 650, 655 has a width (w) from 2.0 μm to 500 μm, for example about 30 μm or about 50 μm.

Figure 6C:
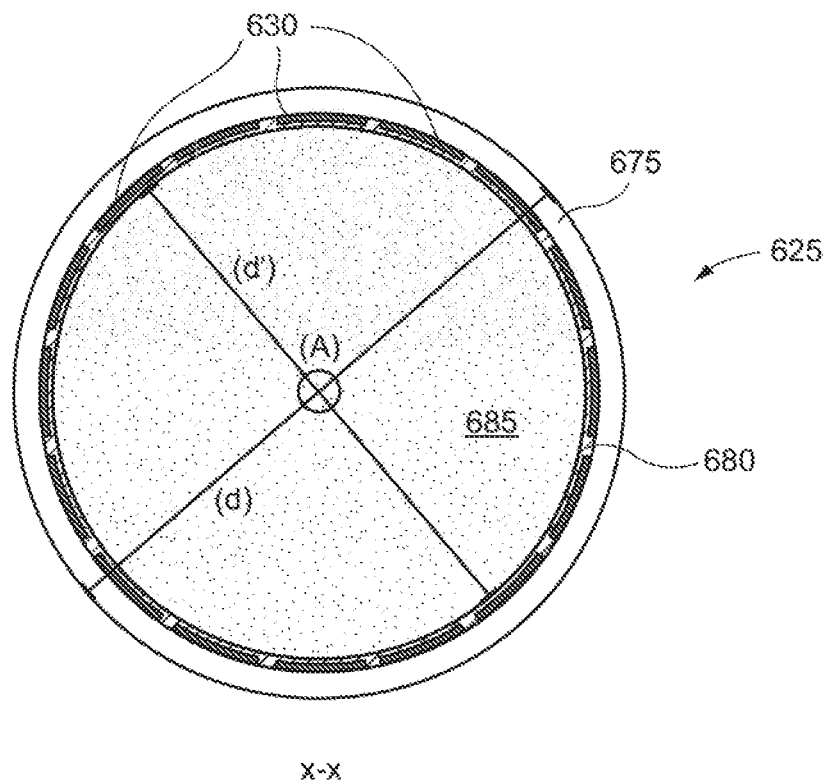

As shown in FIG. 6C (cross-section of the main body 605 along X-X from FIG. 6A), the supporting structure 625 may comprise a first layer of dielectric material 675 and a second layer of dielectric material 680 with the plurality of conductive traces 630 buried between the first layer of dielectric material 675 and the second layer of dielectric material 680. The dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The first layer of dielectric material 675 may be comprised of the same material or a different material from that of the second layer of dielectric material 680. For example, the first layer of dielectric material 675 may be a high temperature liquid crystal polymer, and the second layer of dielectric material 680 may be a low temperature liquid crystal polymer.

As illustrated in FIG. 6C, the main body 305 may be a cylindrical tube. Although the main body 605 is described herein with respect to a cylindrical tube shape, it should be understood that other shapes for the main body 605 have been contemplated, for example, flat (planar), cubed, spherical cubed, torus, ellipsoid, etc. In some embodiments, the cylindrical tube is fabricated with at least the layers of dielectric material 675, 680. For example, the one or more layers of dielectric material 675, 680 may be wrapped in a longitudinal manner around the longitudinal axis (A) or wrapped in a helical manner around the longitudinal axis (A). The first layer of dielectric material 675 may define an outer diameter (d) of the cylindrical tube and the second layer of dielectric material 680 may define an inner diameter (d') of the cylindrical tube. The cylindrical tube may be further fabricated to include a lumen 685 defined by the inner diameter (d'). The lumen 685 may be hollow or may be at least partially filled with one or more layers of material to create a core with hardness measured by a Shore A durometer of greater than 70 A. In some embodiments, the one or more layers of material of the core are polyimide, liquid crystal polymer, parylene, polyether ether ketone, polyurethane, metal, or a combination thereof. In certain embodiments, the one or more layers of material of the core are a thermosetting or thermoplastic polyurethane.

Figure 6D:
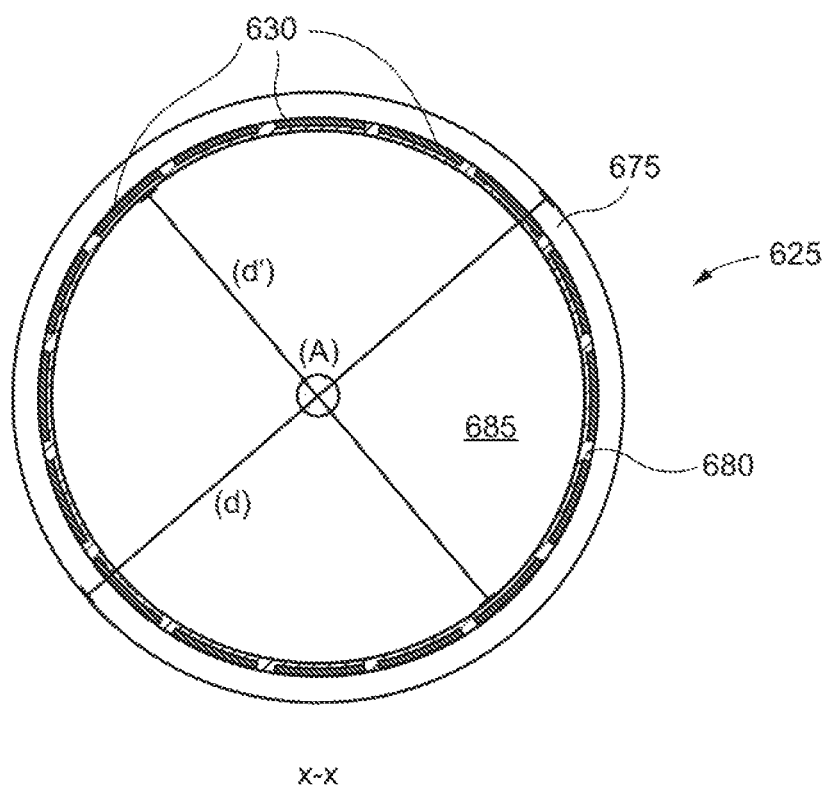

As shown in FIG. 6D (cross-section of a flexible portion or bridge 620 along Y-Y from FIG. 6A), the supporting structure 645 may comprise the first layer of dielectric material 675 and the second layer of dielectric material 680 with the set of conductive traces 655 buried between the first layer of dielectric material 675 and the second layer of dielectric material 680. For example, the supporting structure 640 may be extended to form the supporting structure 645. As with the supporting structure 640, the first layer of dielectric material 675 may be comprised of the same material or a different material from that of the second layer of dielectric material 380. For example, the first layer of dielectric material 675 may be a high temperature liquid crystal polymer, and the second layer of dielectric material 680 may be a low temperature liquid crystal polymer. As illustrated in FIG. 6D, the flexible portion or bridge 320 may be a cylindrical tube. Although the flexible portion or bridge 320 is described herein with respect to a cylindrical tube shape, it should be understood that other shapes for the flexible portion or bridge 320 have been contemplated, for example, flat (planar), cubed, spherical cubed, torus, ellipsoid, etc. In some embodiments, the cylindrical tube is fabricated with at least the layers of dielectric material 675, 680. For example, the one or more layers of dielectric material 675, 680 may be wrapped in a longitudinal manner around the longitudinal axis (A) or wrapped in a helical manner around the longitudinal axis (A). The first layer of dielectric material 675 may define an outer diameter (d) of the cylindrical tube and the second layer of dielectric material 680 may define an inner diameter (d') of the cylindrical tube. The cylindrical tube may be further fabricated to include a lumen 685 defined by the inner diameter (d'). The lumen 685 may be hollow or may be at least partially filled with one or more layers of material to create a core with hardness measured by a Shore A durometer of less than or equal to 70 A. In some embodiments, the one or more layers of material of the core are polyimide, liquid crystal polymer, parylene, polyether ether ketone, polyurethane, metal, or a combination thereof. In certain embodiments, the one or more layers of material of the core are a thermosetting or thermoplastic polyurethane.

Figure 6E:
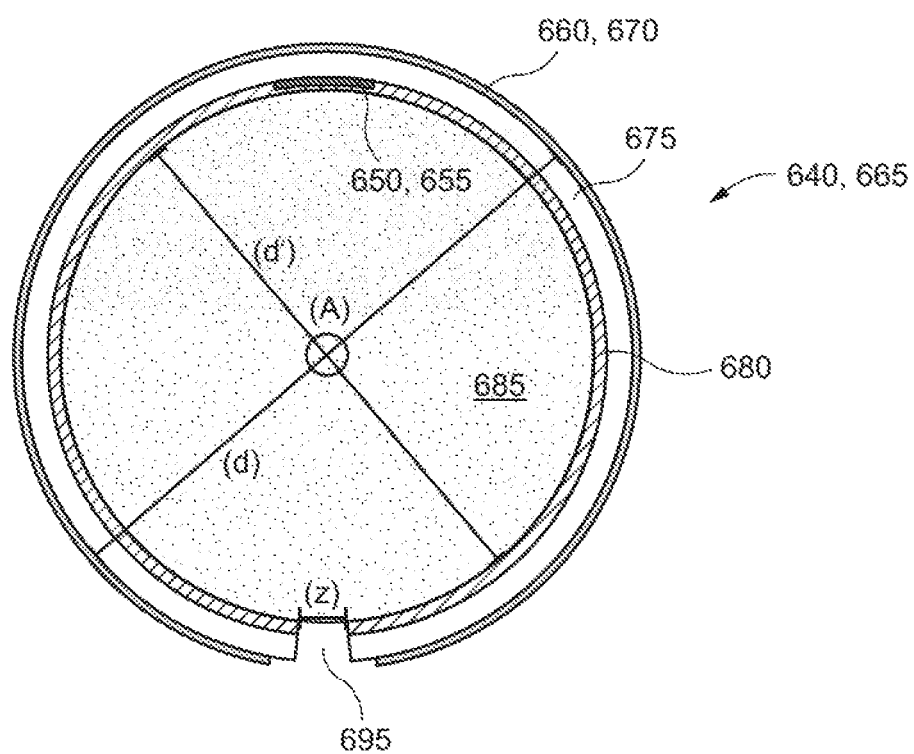

As shown in FIG. 6E (cross-section of the first section 610 along M-M or the second section 615 along W-W from FIG. 6A), the supporting structure 640, 665 may comprise the first layer of dielectric material 675 and the second layer of dielectric material 680 with a set of conductive traces 655 buried between the first layer of dielectric material 675 and the second layer of dielectric material 680. For example, the supporting structure 625 may be extended to form the supporting structure 640 and/or the supporting structure 645 may be extended to form the supporting structure 665. As with the supporting structure 625 and the supporting structure 645, the dielectric material may be selected from the group of electrically flexible nonconductive materials consisting of organic or inorganic polymers, polyimide-epoxy, epoxy-fiberglass, and the like. In certain embodiments, the dielectric material is a thermoplastic or thermosetting polymer. For example, the polymer may be a polyimide, a LCP, silicone, parylene, a PEEK, or combinations thereof. The first layer of dielectric material 675 may be comprised of the same material or a different material from that of the second layer of dielectric material 680. For example, the first layer of dielectric material 675 may be a high temperature liquid crystal polymer, and the second layer of dielectric material 680 may be a low temperature liquid crystal polymer.

As illustrated in FIG. 6E, the first section 610 and the second section 615 may be a cylindrical tube. Although the first section 610 and the second section 615 are described herein with respect to a cylindrical tube shape, it should be understood that other shapes for the first section 610 and the second section 615 have been contemplated, for example, flat (planar), cubed, spherical cubed, torus, ellipsoid, etc. In some embodiments, the cylindrical tube is fabricated with at least the layers of dielectric material 675, 680. For example, the one or more layers of dielectric material 675, 680 may be wrapped in a longitudinal manner around the longitudinal axis (A) or wrapped in a helical manner around the longitudinal axis (A). In some embodiments, the one or more layers of dielectric material 675, 680 are at least partially wrapped around the lumen 685. For example, the one or more layers of dielectric material 675, 680 may be formed as a split cylindrical tube wrapped around the lumen 685, and the split cylindrical tube comprises a gap 695 for the split having a predefined width (z). The predefined width may be between 0.1 mm and 10 mm, for example about 1 mm.

The first layer of dielectric material 675 may define an outer diameter (d) of the cylindrical tube and the second layer of dielectric material 680 may define an inner diameter (d') of the cylindrical tube. The cylindrical tube may be further fabricated to include the lumen 685 defined by the inner diameter (d'). The lumen 685 may be hollow or may be at least partially filled with one or more layers of material to create a core with a hardness measured by a Shore A durometer of greater than 70 A. In some embodiments, the one or more layers of material of the core are polyimide, liquid crystal polymer, parylene, polyether ether ketone, polyurethane, metal, or a combination thereof. In certain embodiments, the one or more layers of material of the core are a thermosetting or thermoplastic polyurethane.

In some embodiments, the conductive contacts 660, 670 are annular rings positioned around the longitudinal axis (A) of the cylindrical tube and exposed on the surface of the cylindrical tube. Each annular ring may be spaced apart from one another on the surface of the cylindrical tube by a region 690 (shown in FIG. 6A) of the first layer of the dielectric material 675. A width (p) of the region 690 of the first layer of the dielectric material 675 that separates each split annular ring may be between 0.1 mm to 6 mm, for example about 0.4 mm. In some embodiments, each annular ring connects to a single trace from the first or second set of conductive traces 650, 655. In other embodiments, each annular ring connects to two or more traces from the first or second set of conductive traces 650, 655. For example, the annular rings may be split and a left side of the split annular ring may be connected with a first trace and a right side of the annular ring may be connected with a second trace. Alternatively, a multiplexer chip may be used to drive signals and thus the annular ring may be connected to multiple traces from the first or second set of conductive traces 650, 655. In various embodiments, eight conductive contacts 660, 670 or annular rings are positioned around the longitudinal axis (A) of each cylindrical tube and exposed on the surface of each cylindrical tube; however, it should be understood that more or less than eight conductive contacts 660, 670 or annular rings can be positioned on the cylindrical tubes. For example, each cylindrical tube can have the same or a different amount of the conductive contacts 660, 670 or split annular rings (1, 2, 3, 4, 5, 6, 7, 8, 9, 10, 11, etc.) to enhance design flexibility for the connector 600.

Figure 7A:
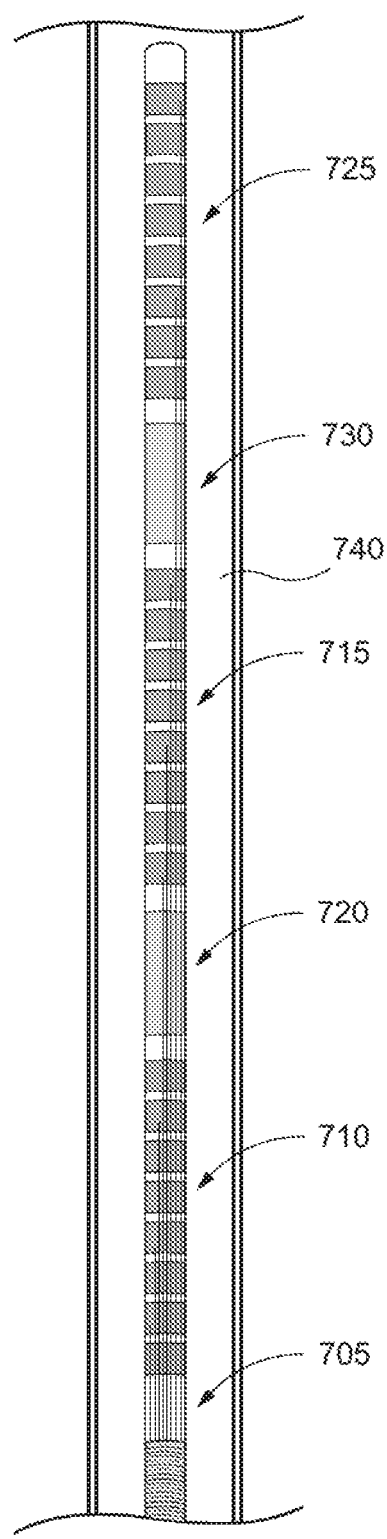
FIGS. 7A-7C show alternative multi-sectioned connectors in various arrangements in accordance with various embodiments.

FIG. 7A shows a connector 700 (e.g., the connector 600 described with respect to FIGS. 6A-6E) comprising a main body 705, a first section 710 (primary section), a second section 715 (secondary section) connected via a flexible portion or bridge 720 to the first section 710, and a third section 725 (another secondary section) connected via a flexible portion or bridge 730 to the second section 715. The connector 700 may be arranged linearly with the main body 705, the first section 710, the second section 715, and the third section 715 arranged in tandem aligned along the longitudinal axis (A) of the main body 705. This arrangement allows a lead assembly with the connector 700 to pass completely through the lumen 730 of a rigid cannula 735, as the main body 705, the first section 710, the second section 715, and the third section 725 are capable of lining up like train cars on a track as the connector 700 passes through the cannula 735 during implant.

Figure 7B:
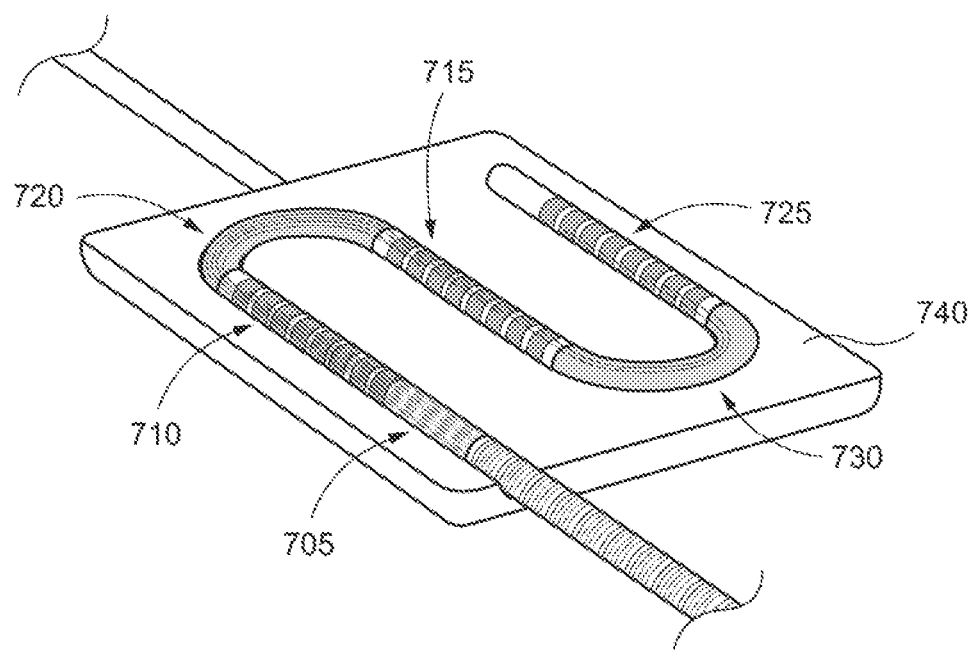

FIG. 7B shows the connector 700 may be arranged in a pattern (e.g., a serpentine pattern) with the second section 715 and the third section 725 disposed in a rational position relative to the first section 710 and one another. For example, after implantation of the lead assembly with the connector 700, withdrawal of the cannula 735, and removal of the stylet (not shown), the connector 700 may be placed in a clamshell receiver 740 that utilizes the flexible portions or bridges 720, 730 to mold the connector 700 in a pattern. In order for the main body 705, the first section 710, the second section 715, and the third section 725 to be molded in a pattern, the flexible portions or bridges 720, 730 are structured to enable the second section 715 and the third section 725 to be placed in various positions or locations within the clam shell receiver 740. In various embodiments, structured means that the flexible portions or bridges 720, 730 have (i) a predetermined degree of flexibility, and/or (ii) a predetermined length (l) that allows the second section 715 and third section 725 to extend beyond the first section 710 and form various patterns (e.g., a serpentine or circular pattern).

In some embodiments, the flexibility of the flexible portions or bridges 720, 730 allows for the flexible portions or bridges 720, 730 to be positioned (e.g., bent) such that the first section 710, the second section 715, and the third section 725 are aligned on a same plane (k). The flexibility of the flexible portions or bridges 720, 730 may be characterized by its hardness and/or elongation of break. In some embodiments, the flexible portions or bridges 720, 730 have a hardness measured by a Shore A durometer of less than 95 A. In some embodiments, the flexible portions or bridges 720, 730 have a hardness measured by a Shore A durometer of equal to or less than 70 A. In certain embodiments, the flexible portions or bridges 720, 730 have a hardness, measured by a Shore A durometer, that is less than the hardness, measured by a Shore A durometer, of the first section 705 and/or the second section 715. In some embodiments, the flexible portions or bridges 720, 730 have an elongation of break of at least 10%. In some embodiments, the flexible portions or bridges 720, 730 have an elongation of break of greater than 100%, up to and including 1000%. In certain embodiments, the elongation of break of the flexible portions or bridges 720, 703 is greater than the elongation of break of the first section 705 and/or the second section 715.

In some embodiments, the length (l) of the flexible portions or bridges 720 allows for the second portion 715 and the third portion 725 to be bent back and positioned alongside of the first section 710 (disposed on a same plane (k) as the first section 710). In certain embodiments, the length (l) of the flexible portions or bridges 720, 730 is greater than at least half the length (l') of at least the first section 710. As should be understood, the length (l) of the flexible portions or bridges 720, 730 may need to be even greater than (l') of the first section 705 to mold various patterns.

Figure 7C:
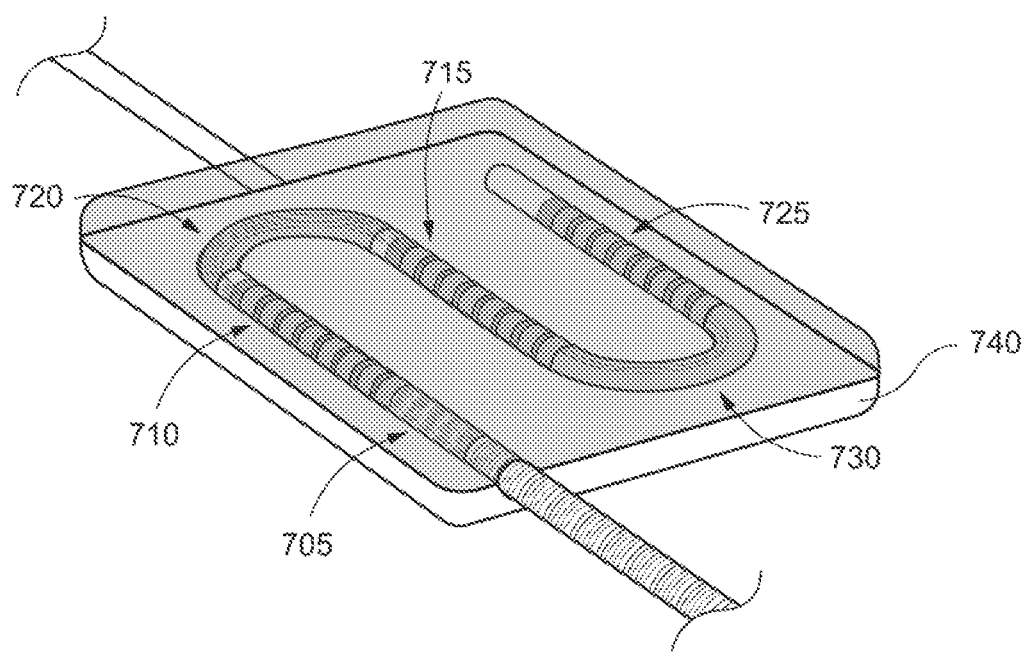

FIG. 7C shows the connector 700 inserted into the clamshell receiver 740 and a lid 750 of the clamshell closed such that the conductive contacts on the first section 710, the second section 715, and the third section 725 make electrical connection with respective conductive contacts within the lid of the clamshell (this ultimately connects the electrodes with the electronics module of the implantable neurostimulator). The electrical connection to the neurostimulator can be direct, for example, the clamshell structure may be integrated as a part of the header of the neurostimulator, or the electrical connection could be indirect, for example, via an extender lead or cable. As shown, upon connection, in some embodiments, the flexible portions or bridges 720, 730 remain internal to the clamshell.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A connector comprising:
a main body comprising a first supporting structure and a plurality of conductive traces formed on the first supporting structure;
a first plug extending from the main body, the first plug comprising:
a second supporting structure,
a first set of conductive traces extending from the plurality of conductive traces and formed on the second supporting structure, and
a first set of conductive contacts formed on the second supporting structure, wherein the first set of conductive contacts is electrically connected to the first set of conductive traces;
a flexible bridge that is branched out from the main body and extends from a side of the main body, the flexible bridge comprising:
a distal end contacting the main body, wherein at least a portion of the flexible bridge that is adjacent the distal end is separated from the main body by a gap in a lengthwise direction of the flexible bridge,
a third supporting structure, and
a second set of conductive traces extending from the plurality of conductive traces and formed on the third supporting structure; and
a second plug extending from a proximal end of the flexible bridge that is disposed opposite the distal end, the second plug comprising:
a fourth supporting structure,
the second set of conductive traces extending from the plurality of conductive traces and formed on the fourth supporting structure, and
a second set of conductive contacts formed on the fourth supporting structure, wherein the second set of conductive contacts is electrically connected to the second set of conductive traces,
wherein the flexible bridge has a length that enables a tandem arrangement of the first plug and the second plug on a longitudinal axis of the main body.

2. The connector of claim 1, wherein:
the second supporting structure and the fourth supporting structure are formed of one or more layers of dielectric material;
the one or more layers of dielectric material comprise a first layer of dielectric material and a second layer of dielectric material;
the first set of conductive traces are buried between the first layer of dielectric material and the second layer of dielectric material of the first plug; and
the second set of conductive traces are buried between the first layer of dielectric material and the second layer of dielectric material of the second plug.

3. The connector of claim 2, wherein:
the first plug and the second plug are each cylindrical tubes; and
each of the cylindrical tubes comprise:
(i) the one or more layers of dielectric material, wherein the first layer of dielectric material defines an outer diameter of the cylindrical tube and the second layer of dielectric material defines an inner diameter of the cylindrical tube; and
(ii) a core that at least partially fills an interior of the cylindrical tube defined by the inner diameter of the cylindrical tube.

4. The connector of claim 3, wherein the one or more layers of dielectric material are at least partially wrapped around the core.

5. The connector of claim 3, wherein the first layer of dielectric material is a high temperature liquid crystal polymer, and the second layer of dielectric material is a low temperature liquid crystal polymer.

6. The connector of claim 3, wherein the core is comprised of one or more layers of material such that the core has a hardness measured by a Shore A durometer of greater than 70A.

7. The connector of claim 1, wherein the third supporting structure is formed of one or more layers of dielectric material and the flexible bridge has a hardness, measured by a Shore A durometer, that is less than a hardness, measured by the Shore A durometer, of the first plug and the second plug.

8. The connector of claim 1, wherein the flexible bridge has a length that is greater than a length of the first plug.

9. The connector of claim 8, wherein the flexible bridge is a helical structure.

10. The connector of claim 9, wherein the flexible bridge is wrapped in a helical manner around the first plug.

11. The connector of claim 9, further comprising a silicone sleeve placed over the flexible bridge.

12. A lead assembly comprising:
a cable comprising a proximal end, a distal end, a first supporting structure, a first set of conductive traces formed on the first supporting structure, and a second set of conductive traces formed on the first supporting structure;
a first plug extending from the proximal end of the cable, wherein the first plug comprises:
a second supporting structure and a first set of conductive contacts formed on the second supporting structure, wherein the first set of conductive contacts is electrically connected to the first set of conductive traces;
a flexible bridge that is branched out from the cable and extends from a side of the cable, wherein the flexible bridge comprises:
a distal end contacting the cable at a region proximate the proximal end of the cable, wherein at least a portion of the flexible bridge that is adjacent the distal end of the flexible bridge is separated from the cable by a gap in a lengthwise direction of the flexible bridge,
a third supporting structure, and
the second set of conductive traces extending from the cable and formed on the third supporting structure; and
a second plug extending from a proximal end of the flexible bridge that is disposed opposite the distal end of the flexible bridge, wherein the second plug comprises:
a fourth supporting structure and a second set of conductive contacts formed on the fourth supporting structure, wherein the second set of conductive contacts is electrically connected to the second set of conductive traces,
wherein the flexible bridge has a length that enables a tandem arrangement of the first plug and the second plug on a longitudinal axis of a main body.

13. The lead assembly of claim 12, further comprising an electrode assembly located at the distal end of the cable, the electrode assembly comprising electrodes electrically connected to the first set of conductive traces and the second set of conductive traces.

14. The lead assembly of claim 12, wherein the first supporting structure, the second supporting structure, the third supporting structure, the fourth supporting structure, or a combination thereof are formed of one or more layers of dielectric material.

15. The lead assembly of claim 12, wherein:
the second supporting structure and the fourth supporting structure are formed of one or more layers of dielectric material;
the one or more layers of dielectric material comprise a first layer of dielectric material and a second layer of dielectric material;
the first set of conductive traces are buried between the first layer of dielectric material and the second layer of dielectric material of the first plug; and
the second set of conductive traces are buried between the first layer of dielectric material and the second layer of dielectric material of the second plug.

16. The lead assembly of claim 15, wherein:
the first plug and the second plug are each cylindrical tubes; and
each of the cylindrical tubes comprise:
(i) the one or more layers of dielectric material, wherein the first layer of dielectric material defines an outer diameter of the cylindrical tube and the second layer of dielectric material defines an inner diameter of the cylindrical tube; and
(ii) a core that at least partially fills an interior of the cylindrical tube defined by the inner diameter of the cylindrical tube.

17. The lead assembly of claim 16, wherein the one or more layers of dielectric material are at least partially wrapped around the core.

18. The lead assembly of claim 16, wherein the first layer of dielectric material is a high temperature liquid crystal polymer, and the second layer of dielectric material is a low temperature liquid crystal polymer.

19. The lead assembly of claim 16, wherein the core is comprised of one or more layers of material such that the core has a hardness measured by a Shore A durometer of greater than 70A.

20. The lead assembly of claim 12, wherein the third supporting structure is formed of one or more layers of dielectric material, and the flexible bridge has a hardness, measured by a Shore A durometer, that is less than a hardness, measured by the Shore A durometer, of the first plug and the second plug.

* * * * *